(12) United States Patent
Herman et al.

(10) Patent No.: US 7,749,709 B2
(45) Date of Patent: Jul. 6, 2010

(54) SOCS-1 GENE METHYLATION IN CANCER

(75) Inventors: James G. Herman, Lutherville, MD (US); Hirohide Yoshikawa, Tokyo (JP); Curtis C. Harris, Garrett Park, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 12/036,182

(22) Filed: Feb. 22, 2008

(65) Prior Publication Data

US 2008/0213782 A1 Sep. 4, 2008

Related U.S. Application Data

(63) Continuation of application No. 10/123,882, filed on Apr. 15, 2002, now Pat. No. 7,348,139.

(60) Provisional application No. 60/283,709, filed on Apr. 13, 2001.

(51) Int. Cl.
C12Q 1/68 (2006.01)

(52) U.S. Cl. .......................................................... 435/6

(58) Field of Classification Search ........................ None
See application file for complete search history.

(56) References Cited

U.S. PATENT DOCUMENTS 6,323,317 B1 * 11/2001 Hilton et al. ................. 530/350

FOREIGN PATENT DOCUMENTS

| WO | WO 99/03993 | 1/1999 |
| WO | WO 99/61614 | 12/1999 |
| WO | WO 00/75326 | 12/2000 |

OTHER PUBLICATIONS

Bai et al., *International Journal of Cancer*, 112(5):846-53 (2004).
Baylin et al., "Abnormal Patterns of DNA Methylation in Human Neoplasia: Potential Consequences for Tumor Progression", *Cancer Cells*, 3(10):383-390 (1991).
Bender et al., "DNA Methylation as a Target for Drug Design", *Pharmaceutical Research*, 15(2):175-187 (1998).
Church et al., *Proc. Natl. Acad. Sci. USA*, 81:1991-1995 (1984).
Esteller et al., "Inactivation of the DNA Repair Gene $0^6$ Methylguanine-DNA Methyltransferase by Promoter Hypermethylation is a Common Event in Primary Human Neoplasia", *Cancer Research*, 59:793-797 (1999).
Garcia et al., "Constitutive Activation of Stat3 in Fibroblasts Transformed by Diverse Oncoproteins and in Breast Carcinoma Cells", *Cell Growth & Differentiation*, 8:1267-1276 (1997).
Guillerm et al., "p16$^{INK4a}$ and p15$^{INK4b}$ Gene Methylations in Plasma Cells from Monoclonal Gammapathy of Undetermined Significance", *Blood*, 98(1):244-246 (2001).
Herman et al., *Proc. Nat. Acad. Sci. USA*, 93:9821-9826 (1996).
Herman et al., "Distinct Patterns of Inactivationf p15$^{INK4b}$ and p16$^{INK4A}$ Characterize the Major Types of Hematological Malignancies", *Cancer Research*, 57:837-841 (1997).
Herman et al., "Hypermethylation-Associated Inactivation Indicates a Tumor Suppressor Role for p15$^{INK4B1}$", *Cancer Research*, 56:722-727 (1996).
Herman et all., "Silencing of the VHLTumor-Suppressor Gene by DNA Methylation in Renal Carcinoma", *Proc. Natl. Acad. Sci. USA*, 91:9700-9704 (1994).
InvivoGen, Suppressor of Cytokine Signaling (SOCS), www.invivogen.com/genedescription/socs.htm, Mar. 26, 2002 (date viewed/printed).
Kramer et al., "Extended Analysis of the Region Encompassing the PRM1→PRM2→TNP2 Domain: Genomic Organization, Evolution and Gene Identification", *The Journal of Experimental Zoology*, 282:245-253 (1998).
Makos et al., "Distinct Hypermethylation Patterns Occur at Altered Chromosome Loci in Human Lung and Colon Cancer", *Proc. Natl. Acad. Sci. USA*, 89:1929-1933 (1992).
Makos et al., "Regional DNA Hypermethylation at D17S5 Precedes 17p Structural Changes in the Progression of Renal Tumors", *Cancer Research*, 53:2719-2722 (1993).
Makos et al, "DNA Hypermethylation is Associated with 17p Allelic Loss in Neural Tumors", *Cancer Research*, 53:2715-2718 (1993).
Margaret et al., "Frequent Death-Associated Protein Kinase Promoter Hypermethylation in Multiple Myeloma", *Clinical Cancer Research*, 7:1724-1729 (2001).
Masuhara et al., "Cloning and Characterization of Novel CIS Family Genes", *Biochemical and Biophysical Research Communications*, 239; 439-446, Article No. RC977484 (1997).
Nagai et al., *J. Hepatol.*, 34:416-421 (2001).
Nagai et al., "Aberration of Genomic DNA in Association with Human Hepatocellular Carcinomas Detected by 2-Dimensional Gel Analysis", *Cancer Research*, 54:1545-1550 (1994).
Naka et al., "Structure and Function of a New STAT-Induced STAT Inhibitor", *Nature*, 387:924-929 (1997).
Pogribny et al., *Biochem. Biophys. Res. Commun.*, 262(3):624-628 (1999).
Rein et al., "Absence of an unusual "densely methylated island" at the hamster dhfr ori-beta",*J. Biol. Chem.*, 272:10021-10029 (1997).
Starr et al., "A Family of Cytokine-Inducible Inhibitors of Signalling", *Nature*, 387:917-921 (1997).
Voet et al., *Biochemistry*, Chapter 28. Nucleic Acid Structures & Manipulation, John Wiley & Sons, p. 831 only (1990).
Yoshikawa et al., "SOCS-1, A Negative Regulator of the JAK/STAT Pathway, is Silenced by Methylation in Human Hepatocellular Carcinoma and Shows Growth-Suppression Activity", *Nature Genetics*, 28:29-35 (2001).
Yoshikawa et al., "Chromosome Assignment of Aberrant NotI Restriction DNA Fragments in Primary Hepatocellular Carcinoma", *Gene*, 197:129-135 (1997).

* cited by examiner

*Primary Examiner*—Misook Yu
(74) *Attorney, Agent, or Firm*—DLA Piper LLP (US)

(57) ABSTRACT

Methods are provided for identifying a cell exhibiting unregulated growth associated with methylation-silenced transcription of a suppressor of cytokine signaling (SOCS)/cytokine-inducible SH2 protein (CIS) family member (SOCS/CIS) gene such as the SOCS-1 gene. In addition, methods of treating a cancer patient, wherein cancer cells in the patient exhibit methylation-silenced transcription of SOCS/CIS gene such as a SOCS-1 gene, are provided, as are reagents for practicing such methods.

4 Claims, No Drawings

```
                         SEQUENCE LISTING

<160> NUMBER OF SEQ ID NOS: 20

<210> SEQ ID NO 1
<211> LENGTH: 1094
<212> TYPE: DNA
<213> ORGANISM: Homo sapiens

<400> SEQUENCE: 1
ctccggctgg ccccttctgt aggatggtag cacacaacca ggtggcagcc gacaatgcag      60
tctccacagc agcagagccc cgacggcggc cagaaccttc ctcctcttcc tcctcctcgc     120
ccgcggcccc cgcgcgcccg cggccgtgcc ccgcggtccc ggccccggcc cccggcgaca     180
cgcacttccg cacattccgt tcgcacgccg attaccggcg catcacgcgc gccagcgcgc     240
tcctggacgc ctgcggattc tactggggc ccctgagcgt gcacggggcg cacgagcggc      300
tgcgcgccga gcccgtgggc accttcctgg tgcgcgacag ccgccagcgg aactgctttt     360
tcgcccttag cgtgaagatg gcctcgggac ccacgagcat ccgcgtgcac tttcaggccg     420
gccgctttca cctggatggc agccgcgaga gcttcgactg cctcttcgag ctgctggagc     480
actacgtggc ggcgccgcgc cgcatgctgg gggccccgct gcgccagcgc cgcgtgcggc     540
cgctgcagga gctgtgccgc cagcgcatcg tggccaccgt gggccgcgag aacctggctc     600
gcatccccct caacccccgtc ctccgcgact acctgagctc cttcccctcc cagatttgac     660
cggcagcgcc cgccgtgcac gcagcattaa ctgggatgcc gtgttatttt gttattactt     720
gcctggaacc atgtgggtac cctccccggc ctgggttgga gggagcggat gggtgtaggg     780
gcgaggcgcc tcccgccctc ggctggagac gaggccgcag accccttctc acctcttgag     840
ggggtcctcc ccctcctggt gctccctctg ggtcccctg gttgttgtag cagcttaact     900
gtatctggag ccaggacctg aactcgcacc tcctacctct tcatgtttac atatacccag     960
```

-continued

```
tatctttgca caaaccaggg gttgggggag ggtctctggc tttatttttc tgctgtgcag    1020
aatcctattt tatattttt aaagtcagtt taggtaataa actttattat gaaagttttt    1080
ttttttaaaa aaaa                                                      1094
```

<210> SEQ ID NO 2
<211> LENGTH: 24
<212> TYPE: DNA
<213> ORGANISM: Artificial sequence
<220> FEATURE:
<223> OTHER INFORMATION: Forward primer

<400> SEQUENCE: 2
ttcgcgtgta tttttaggtc ggtc                                           24

<210> SEQ ID NO 3
<211> LENGTH: 23
<212> TYPE: DNA
<213> ORGANISM: Artificial sequence
<220> FEATURE:
<223> OTHER INFORMATION: Reverse primer

<400> SEQUENCE: 3
cgacacaact cctacaacga ccg                                            23

<210> SEQ ID NO 4
<211> LENGTH: 33
<212> TYPE: DNA
<213> ORGANISM: Artificial sequence
<220> FEATURE:
<223> OTHER INFORMATION: Forward primer

<400> SEQUENCE: 4
ttatgagtat ttgtgtgtat ttttaggttg gtt                                 33

<210> SEQ ID NO 5
<211> LENGTH: 29
<212> TYPE: DNA
<213> ORGANISM: Artificial sequence
<220> FEATURE:
<223> OTHER INFORMATION: Reverse Primer

<400> SEQUENCE: 5
cactaacaac acaactccta caacaacca                                      29

<210> SEQ ID NO 6
<211> LENGTH: 29
<212> TYPE: DNA
<213> ORGANISM: Artificial sequence
<220> FEATURE:
<223> OTHER INFORMATION: Amplification primer

<400> SEQUENCE: 6
tgtaggatgg tagtatataa ttaggtggt                                      29

<210> SEQ ID NO 7
<211> LENGTH: 29
<212> TYPE: DNA
<213> ORGANISM: Artificial sequence
<220> FEATURE:
<223> OTHER INFORMATION: Amplification primer

<400> SEQUENCE: 7
taatactcca acaactctaa aaacaatc                                       29

```
<210> SEQ ID NO 8
<211> LENGTH: 19
<212> TYPE: DNA
<213> ORGANISM: Artificial sequence
<220> FEATURE:
<223> OTHER INFORMATION: PCR primer

<400> SEQUENCE: 8
aacaccccag ccatgtacg                                                  19

<210> SEQ ID NO 9
<211> LENGTH: 19
<212> TYPE: DNA
<213> ORGANISM: Artificial sequence
<220> FEATURE:
<223> OTHER INFORMATION: PCR primer

<400> SEQUENCE: 9
atgtcacgca cgatttccc                                                  19

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
cagcccagag gagcctaaag                                                 20

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
tccagttcag ggtgccatac                                                 20

<210> SEQ ID NO 12
<211> LENGTH: 19
<212> TYPE: DNA
<213> ORGANISM: Artificial sequence
<220> FEATURE:
<223> OTHER INFORMATION: PCR primer

<400> SEQUENCE: 12
ttctctcacc ccctcacgc                                                  19

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
gctgggcact tggttactgg                                                 20

<210> SEQ ID NO 14
<211> LENGTH: 20
<212> TYPE: DNA
<213> ORGANISM: Artificial sequence
<220> FEATURE:
<223> OTHER INFORMATION: PCR primer
```

<400> SEQUENCE: 14 cccctctgt aggatggtag                                                    20

<210> SEQ ID NO 15
<211> LENGTH: 20
<212> TYPE: DNA
<213> ORGANISM: Artificial sequence
<220> FEATURE:
<223> OTHER INFORMATION: PCR primer

<400> SEQUENCE: 15
catcccagtt aatgctgcgt                                                   20

<210> SEQ ID NO 16
<211> LENGTH: 20
<212> TYPE: DNA
<213> ORGANISM: Artificial sequence
<220> FEATURE:
<223> OTHER INFORMATION: Sense primer

<400> SEQUENCE: 16
cccggagcat gcgcgagagc                                                   20

<210> SEQ ID NO 17
<211> LENGTH: 20
<212> TYPE: DNA
<213> ORGANISM: Artificial sequence
<220> FEATURE:
<223> OTHER INFORMATION: Antisense primer

<400> SEQUENCE: 17
tgcgggctct gctgctgtgg                                                   20

<210> SEQ ID NO 18
<211> LENGTH: 21
<212> TYPE: DNA
<213> ORGANISM: Artificial sequence
<220> FEATURE:
<223> OTHER INFORMATION: Sense primer

<400> SEQUENCE: 18
gaccacagtc catgccatca c                                                 21

<210> SEQ ID NO 19
<211> LENGTH: 21
<212> TYPE: DNA
<213> ORGANISM: Artificial sequence
<220> FEATURE:
<223> OTHER INFORMATION: Antisense sequence

<400> SEQUENCE: 19
gtccaccacc ctgttgctgt a                                                 21

<210> SEQ ID NO 20
<211> LENGTH: 211
<212> TYPE: PRT
<213> ORGANISM: Homo sapiens

<400> SEQUENCE: 20

Met Val Ala His Asn Gln Val Ala Ala Asp Asn Ala Val Ser Thr Ala
1               5                   10                  15

Ala Glu Pro Arg Arg Arg Pro Glu Pro Ser Ser Ser Ser Ser Ser
            20                  25                  30

Pro Ala Ala Pro Ala Arg Pro Arg Pro Cys Pro Ala Val Pro Ala Pro

-continued

```
                35                  40                  45
Ala Pro Gly Asp Thr His Phe Arg Thr Phe Arg Ser His Ala Asp Tyr
    50                  55                  60

Arg Arg Ile Thr Arg Ala Ser Ala Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
                100                 105                 110

Phe Ala Leu Ser Val Lys Met Ala Ser Gly Pro Thr Ser Ile Arg Val
            115                 120                 125

His Phe Gln Ala Gly Arg Phe His Leu Asp Gly Ser Arg Glu Ser Phe
        130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
            180                 185                 190

Arg Ile Pro Leu Asn Pro Val Leu Arg Asp Tyr Leu Ser Ser Phe Pro
        195                 200                 205

Phe Gln Ile
        210
```

SOCS-1 GENE METHYLATION IN CANCER

CROSS REFERENCE TO RELATED APPLICATIONS

This application is a continuation application of U.S. application Ser. No. 10/123,882 filed Apr. 15, 2002, now U.S. Pat. No. 7,348,139; which claims the benefit under 35 USC §119 (e) to U.S. Application Ser. No. 60/283,709 filed Apr. 13, 2001, now abandoned. The disclosure of each of the prior applications is considered part of and is incorporated by reference in the disclosure of this application.

GRANT INFORMATION

This invention was made with government support under Grant No. CA 58184 awarded by the National Cancer Institute. The government has certain rights in this invention.

BACKGROUND OF THE INVENTION

1. Field of the Invention

The present invention relates generally to an epigenetic marker indicative of cancer, and more specifically to the identification of a correlation of methylation-silenced transcription of SOCS-1 gene expression and cancer, and to reagents and methods for detecting and treating a cancer associated with methylation-silenced transcription of SOCS-1 gene expression.

2. Background Information

Cancer can occur due to contact with various etiologic agent, including, for example, exposure to environmental carcinogens or infection by a virus, or can be acquired congenitally from one or both parents. Such cancers have a genetic basis in that the changes responsible for the cancer are at the level of the nucleotide sequence of one or more genes in an individual. For example, some viruses have a life cycle that includes a stage in which it integrate into the nuclear genome of an organism such as a human. Where such integration results in disruption of a gene that is involved, for example, in instructing a cell to stop proliferating, the result can be unregulated proliferation of the cell, as is characteristic of some cancer cells.

In comparison, chemical carcinogens can cause physical damage to the DNA in an individual. Where the damage caused by the carcinogen is minimal, DNA repair mechanisms often can repair the damage such that the repaired sequence is identical to the sequence prior to the damage. Where the damage caused by the carcinogen is extensive, the cell containing the damaged DNA often dies. In some cases, however, the damage is not sufficient to kill the cell, but is too extensive to be repaired properly. In such cases, while the effort by the cell to repair the damaged DNA can be sufficient for the cell to continue growing and dividing, the repaired sequence is different from the DNA sequence prior to the damage. Where the defective repair occurs in a gene, the product of that gene may not be produced or, if the gene product is produced, it may not function properly. As such, where the normal gene product may, for example, regulate the time the cell normally would be destined to die, a cell lacking the normal gene product, as well as progeny of the cell, may continue to proliferate in an unregulated manner, as is characteristic of some cancer cells.

In addition to such genetic changes, cancer also can be caused by epigenetic mechanisms, which do not result in mutations of the DNA sequence. The most commonly observed epigenetic mechanism involves silencing of gene expression due to methylation of the gene sequence. Methylation of cytosine residues located 5' to guanosine in CpG dinucleotides, particularly in CpG-rich regions (CpG islands), often is involved in the normal regulation of gene expression in higher eukaryotes. For example, extensive methylation of CpG islands is associated with transcriptional inactivation of selected imprinted genes, as well as the genes on the inactivated X chromosome in females. Aberrant methylation of normally unmethylated CpG islands also has been found in immortalized and transformed cells, and has been associated with transcriptional inactivation of defined tumor suppressor genes in human cancers.

Changes to genes that are associated with cancer, including mutations that result in loss of expression of gene or expression of a defective gene product, and epigenetic mechanisms such as methylation-silencing of gene transcription, provide markers useful for determining whether a cell is susceptible to loss of normal growth control and, therefore, potentially a cancer cell. For example, a mutation of the BRCA1 gene has been associated with breast cancer. As such, diagnostic tests can be performed using cells, for example, from a woman with a family history of breast cancer to determine whether the woman has the BRCA1 mutation that is a marker for breast cancer. The prostate specific antigen (PSA) is another example of a marker, in this case for prostate cancer. Although neither the defect resulting in expression of the PSA nor the normal function of PSA in the body is known, PSA nevertheless provides a valuable cancer marker because it allows the identification of men predisposed to prostate cancer or at a very early stage of the disease such that effective therapy can be implemented.

Cancer often is a silent disease that does not present clinical signs or symptoms until the disease is well advance. As such, the use of markers that allow the identification of individuals susceptible to a cancer, or even that allow detection of a cancer at an early stage, can be of great benefit. Unfortunately, such markers are not available for most cancers. As such, many cancer patients do not seek medical assistance until the cancer is at a stage that requires radical therapy, or is untreatable. Thus, a need exists for markers that can be used to detect cancer cells. The present invention satisfies this need and provides additional advantages.

SUMMARY OF THE INVENTION

The present invention is based on the identification of a correlation of unregulated cell growth as occurs in various cancers, and methylation-silenced transcription of a suppressor of cytokine signaling (SOCS)/cytokine-inducible SH2 protein (CIS) family member (SOCS/CIS) gene. This correlation is exemplified by the demonstration that methylation-silenced transcription of the SOCS-1 gene is found in various cancers, including hepatocellular carcinoma, multiple myeloma, and acute leukemias, and that methods and reagents that restore SOCS-1 gene expression is such cancer cells result in apoptosis of the cancer cell. As such, the present invention provides methods of diagnosing a cancer by detecting methylation-silenced transcription of a SOCS/CIS gene, as well as methods of treating such cancers.

The present invention relates to a method for identifying a cell that exhibits, or is predisposed to exhibiting, unregulated growth. Such a method can be performed by detecting methylation of a cytosine residue in a CpG dinucleotide in a CpG island of a SOCS/CIS gene in a test cell, or an extract comprising nucleic acid molecules of the test cell, wherein the SOCS/CIS gene methylation results in a reduced level of transcription of the gene in the test cell as compared to a corresponding normal cell, i.e., a corresponding cell that exhibits normal regulated growth. The SOCS/CIS gene can be a gene encoding any member of the SOCS/CIS family of protein, including, for example, a SOCS gene such as a SOCS-1, SOCS-2 (also called STATI2) or SOCS-3 gene, or a cytokine-inducible SH2 protein-2 (CIS2) gene.

The cell exhibiting, or predisposed to exhibiting, unregulated growth generally, but not necessarily, is a neoplastic cell, which can be a premalignant cell or a malignant cell, i.e., a cancer cell, for example, a hepatocellular carcinoma cell, a multiple myeloma cell, or an acute leukemia cell. The test cell can be any cell, including, for example, a primary cell that has been obtained from a subject and is placed in culture or is being adapted to grow in culture, wherein a method of the invention provides a means to determine whether the cell has maintained regulated growth control and, therefore, following expansion, is suitable for readministration to the subject. The test cell also can be a cell that is obtained from a subject, for example, a cell obtained from an organ sample, a tissue sample, or a cell sample, which can be obtained by a biopsy procedure. As such, the test cell can be a cell from a liver sample, a skin sample, a lymph node sample, a kidney sample, a lung sample, a muscle sample, a bone sample, or a brain sample. The cell also can be a component of a biological fluid, for example, bone marrow, blood, lymph, cerebrospinal fluid, saliva, sputum, stool, urine, or ejaculate. A method of the invention also can be practiced using an extract of a test cell, wherein the extract includes nucleic acid molecules of the test cell, particularly genomic DNA.

Methylation of a CpG dinucleotide in a CpG island of a SOCS/CIS gene can be detected using any of various well known methods for detecting CpG methylation of a nucleic acid molecule. For example, such methylation can be detected by contacting a nucleic acid molecule, which includes all or a portion of a CpG island of the SOCS/CIS gene sequence, with a methylation sensitive restriction endonuclease. The methylation sensitive restriction endonuclease can be one that cleaves a recognition site containing a methylated cytosine residue of a CpG dinucleotide in the SOCS/CIS gene sequence, for example, a restriction endonuclease such as Acc III, Ban I, BstN I, Msp I, or Xma I, whereby cleavage of the nucleic acid molecule indicates that the SOCS/CIS gene in the test cell is methylated. Conversely, the methylation sensitive restriction endonuclease can be one that cleaves a recognition site containing a CpG dinucleotide in the SOCS/CIS gene sequence only when the cytosine residue of the CpG dinucleotide is unmethylated, for example, a restriction endonuclease such as Acc II, Ava I, BssH II, BstU I, Hpa II, or Not I, whereby a lack of cleavage of the nucleic acid molecule indicates that SOCS/CIS gene in the test cell is methylated.

Methylation of a CpG dinucleotide in a CpG island of a SOCS/CIS gene also can be detected by contacting a nucleic acid molecule comprising the SOCS/CIS gene of the test cell with a chemical reagent that selectively modifies either an unmethylated cytosine residue or a methylated cytosine residue, and detecting a product generated due to contact with the reagent, wherein the product is indicative of the methylation status of a cytosine residue in a CpG dinucleotide of the SOCS/CIS gene sequence, i.e., whether the cytosine residue is methylated or unmethylated. Depending on the particular chemical reagent used in such a method and, therefore, the effect that the reagent has on a SOCS/CIS gene sequence containing a methylated or unmethylated cytosine residue in a CpG dinucleotide, the product generated according to the method, which generally is a nucleic acid product that can, but need not, contain a modified nucleotide, can be detected, for example, by sequencing the product, or by a method such as electrophoresis, chromatography, mass spectrometry, or a combination thereof.

In one embodiment, the chemical reagent used in a method of the invention is hydrazine, thereby producing a hydrazine treated SOCS/CIS gene sequence. Where the chemical reagent is hydrazine, the method of detecting CpG dinucleotide methylation of a SOCS/CIS gene sequence further includes contacting the hydrazine treated SOCS/CIS gene sequence with a reagent such as piperidine, which cleaves the nucleic acid molecule at hydrazine modified cytosine residues to generate a product comprising fragments of the SOCS/CIS gene sequence; separating the fragments according to molecular weight, and detecting a gap in the fragment separation pattern at a position known to contain a cytosine residue in a SOCS/CIS gene sequence, wherein the gap is indicative of methylation of a cytosine residue in the CpG dinucleotide in the SOCS/CIS gene of the test cell.

In another embodiment, the chemical reagent used in a method of the invention is a composition comprising bisulfite ions, for example, sodium bisulfite, whereby unmethylated cytosine residues in the SOCS/CIS gene sequence are converted to bisulfite modified cytosine residues. Where the chemical reagent comprises bisulfite ions, the method of detecting CpG dinucleotide methylation of a SOCS/CIS gene sequence further includes exposing the bisulfite ion treated SOCS/CIS gene sequence to alkaline conditions, whereby bisulfite modified cytosine residues are converted to uracil residues; and detecting the amount or distribution of uracil residues in the bisulfite ion treated SOCS/CIS gene of the test cell, wherein a decrease in the amount or distribution of uracil residues in the SOCS/CIS gene from the test cell, as compared to the amount or distribution of uracil residues in a corresponding bisulfite ion treated unmethylated SOCS/CIS gene following exposure to alkaline conditions, is indicative of methylation of cytosine residues in CpG dinucleotides in the SOCS/CIS gene of the test cell.

The amount or distribution of uracil residues produced according to such a method can be detected using any of various methods. For example, the amount or distribution of uracil residues can be detected by sequencing the bisulfite modified SOCS/CIS gene sequence following exposure to alkaline conditions, and identifying uracil residues in the sequence. The amount or distribution of uracil residues also can be detected by contacting the bisulfite ion treated SOCS/CIS gene sequence, following exposure to alkaline conditions, with an oligonucleotide that selectively hybridizes to a SOCS/CIS gene sequence containing uracil residues, and detecting selective hybridization of the oligonucleotide. Selective hybridization of the oligonucleotide can be detected, for example, by performing the method using an oligonucleotide that includes a detectable label (e.g., a radioisotope, a paramagnetic isotope, a luminescent compound, a chemiluminescent compound, a fluorescent compound, a metal chelate, an enzyme, a substrate for an enzyme, a receptor, or a ligand for a receptor) and detecting the label in a hybridization product or a derivative thereof. Selective hybridization also can be detected, for example, by utilizing the oligonucleotide as a substrate for a primer extension reaction, and detecting a product of the primer extension reaction.

The amount or distribution of uracil residues in a bisulfite ion treated SOCS/CIS gene sequence following exposure to alkaline conditions also can be detected using an amplification reaction, for example, a polymerase chain reaction (PCR). In one embodiment, the amplification is performed by contacting the SOCS/CIS gene sequence with an amplification primer pair comprising a forward primer and a reverse primer under conditions suitable for amplification, wherein at least one primer of the primer pair comprises an oligonucleotide that selectively hybridizes to a SOCS/CIS gene sequence containing uracil residues, whereby generation of an amplification product is indicative of methylation of cytosine residues in CpG dinucleotides in the SOCS/CIS gene of the test cell. In another embodiment, the amplification reaction is performed by contacting the SOCS/CIS gene sequence with an amplification primer pair comprising a forward primer and a reverse primer under conditions suitable for amplification, wherein both primers of the primer pair selectively hybridize to a SOCS/CIS gene sequence containing cytosine residues, but not to a SOCS/CIS gene sequence containing uracil residues, whereby generation of an amplification product is indicative of a lack of methylation of cytosine residues in CpG dinucleotides in the SOCS/CIS gene of the test cell.

In still another embodiment, the amplification reaction for detecting the amount or distribution of uracil residues in a bisulfite ion treated SOCS/CIS gene following alkaline treatment is performed by contacting the SOCS/CIS gene sequence with a first amplification primer pair and a second amplification primer pair under conditions suitable for amplification, wherein the first amplification primer pair is a methylation-specific primer pair comprising a forward primer and a reverse primer, wherein at least one primer of the first primer pair comprises an oligonucleotide that selectively hybridizes to a SOCS/CIS gene sequence containing uracil residues, and wherein the second amplification primer pair is an unmethylation-specific primer pair comprising a forward primer and a reverse primer, wherein both primers of the second primer pair selectively hybridize to a SOCS/CIS gene sequence containing cytosine residues, but not to a SOCS/CIS gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the SOCS/CIS gene of the test cell.

The methods of the invention are particularly adaptable to being performed in a high throughput format, wherein a plurality of test cells, or extracts of the test cells, or test cells and extracts thereof are examined sequentially, in parallel, or a combination thereof. Each of the test cells, or extracts of the test cells, of a plurality being examined can the same or different, or can be a combination thereof. For example, the method can be practiced using duplicate or triplicate samples of each of two or more different test cells, i.e., test cells obtained from different subjects or from different sites of a single subject, for example, from a site of a cancer, or a site adjacent to a cancer, or a surgical margin remaining after removal of a cancer; and, if desired, can further include cells that correspond to the test cells, but exhibit normally regulated growth, such cells providing controls or standards with which to compare results obtained for a test cell. Generally, the plurality of test cells, or extracts of the test cells, are arranged in an array, particularly an addressable array, thus providing a means to correlate a result with the source of the test cells. An array can be produced on a microchip, a glass slide, a bead, or other such solid support that allows each sample in the array to be substantially isolated from each other sample, and conveniently can be used in an automated system for adding or removing reagents for practicing the method or for detecting a result of the method.

The present invention also relates to method for identifying a neoplastic cell, which exhibits unregulated growth. Such a method can be performed by detecting methylation of a cytosine residue of a CpG dinucleotide in a CpG island of a suppressor of cytokine signaling-1 (SOCS-1) gene in a sample comprising a test cell, or an extract thereof, whereby methylation of the SOCS-1 gene results in a reduced level of transcription and, therefore, expression of the SOCS-1 gene product in the test cell as compared to a corresponding normal cell.

The neoplastic cell can be a premalignant cell or a malignant cell, i.e., a cancer cell, for example, a hepatocellular carcinoma cell, a multiple myeloma cell, or an acute leukemia cell. The sample to be examined according to a method of the invention can be a sample obtained from a subject such as a human subject, a domesticated animal, a farm animal, or the like, and can be any sample containing a cell suspected of being a neoplastic cell, or containing nucleic acid molecules including a SOCS-1 gene sequence or a portion thereof comprising a CpG island. As such, the sample can be an organ sample, a tissue sample, or a cell sample, for example, a liver sample, a skin sample, a lymph node sample, a kidney sample, a lung sample, a muscle sample, a bone sample, or a brain sample; or can be a sample of a biological fluid, for example, bone marrow, blood, serum, lymph, cerebrospinal fluid, saliva, sputum, stool, urine, or ejaculate.

Methylation of a CpG dinucleotide in a SOCS-1 gene can be detected by contacting a nucleic acid molecule comprising the SOCS-1 gene of the test cell with a methylation sensitive restriction endonuclease that cleaves a recognition site comprising a methylated cytosine residue comprising a CpG dinucleotide, whereby cleavage of the nucleic acid molecule is indicative of methylation of the SOCS-1 gene in the test cell, or with a methylation sensitive restriction endonuclease that does not cleave a recognition site comprising a methylated cytosine residue comprising a CpG dinucleotide, whereby a lack of cleavage of the nucleic acid molecule is indicative of methylation of the SOCS-1 gene in the test cell.

Methylation of a CpG dinucleotide in a SOCS-1 gene also can be detected by contacting a nucleic acid molecule comprising the SOCS-1 gene of the test cell with a chemical reagent that selectively modifies either an unmethylated cytosine residue or a methylated cytosine residue. For example, the chemical reagent can be hydrazine, wherein the method further includes contacting the hydrazine treated SOCS-1 gene sequence with an agent that cleaves hydrazine modified cytosine residues to produce fragments; separating the fragments according to molecular weight; and detecting a gap at a position known to contain a cytosine residue in a SOCS-1 gene sequence, wherein the gap is indicative of methylation of a cytosine residue in the CpG dinucleotide in the SOCS-1 gene of the test cell. The chemical reagent also can be sodium bisulfite, wherein the method further includes exposing the sodium bisulfite ion treated SOCS-1 gene sequence to alkaline conditions, whereby bisulfite modified cytosine residues are converted to uracil residues; and detecting the amount or distribution of uracil residues in the bisulfite ion treated SOCS-1 gene of the test cell, wherein a decrease in the amount or distribution of uracil residues in the SOCS-1 gene from the test cell, as compared to the amount or distribution of uracil residues in a corresponding bisulfite ion treated unmethylated SOCS-1 gene following exposure to alkaline conditions, is indicative of methylation of cytosine residues in CpG dinucleotides in the SOCS-1 gene of the test cell.

The amount or distribution of uracil residues can be detected, for example, by determining the nucleotide sequence of the bisulfite ion treated SOCS-1 gene sequence following exposure to alkaline conditions. The bisulfite ion treated SOCS-1 gene sequence can be determined directly, or can be amplified using an amplification primer pair, for example, an amplification primer pair selected from SEQ ID NO:6 and SEQ ID NO:7; SEQ ID NO:12 and SEQ ID NO:13; SEQ ID NO:14 and SEQ ID NO:15; and SEQ ID NO:16 and SEQ ID NO:17, and the nucleotide sequence of the amplification product can be determined.

The amount or distribution of uracil residues also can be detected by contacting the sodium bisulfite treated SOCS-1 gene sequence, following exposure to alkaline conditions, with an oligonucleotide that selectively hybridizes to a SOCS-1 gene sequence containing uracil residues, for example, an oligonucleotide as set forth in SEQ ID NO:2, and detecting selective hybridization of the oligonucleotide. The amount or distribution of uracil residues also can be detected by contacting the SOCS-1 gene sequence with a methylation-specific amplification primer pair comprising a forward primer and a reverse primer under conditions suitable for amplification, wherein at least one of the forward primer and the reverse primer comprises an oligonucleotide that selectively hybridizes to a SOCS-1 gene sequence containing uracil residues, for example, the primer pair set forth as SEQ ID NO:2 and SEQ ID NO:3, whereby generation of an amplification product is indicative of methylation of cytosine residues in CpG dinucleotides in the SOCS-1 gene of the test cell, thereby identifying the test cell as a neoplastic cell; or by contacting the SOCS-1 gene sequence with an unmethylation-specific amplification primer pair comprising a forward primer and a reverse primer under conditions suitable for amplification, wherein both the forward primer and the reverse primer selectively hybridize to a SOCS-1 gene sequence containing cytosine residues, but not to a SOCS-1 gene sequence containing uracil residues, for example the primer pair set forth as SEQ ID NO:4 and SEQ ID NO:5, whereby generation of an amplification product is indicative of a lack of methylation of cytosine residues in CpG dinucleotides in the SOCS-1 gene of the test cell, thereby identifying the test cell as a neoplastic cell.

Similarly, the amount or distribution of uracil residues can be detected by contacting the SOCS-1 gene sequence with at least two amplification primer pairs, including a methylation-specific amplification primer pair, for example, SEQ ID NO:2 and SEQ ID NO:3, and an unmethylation-specific amplification primer pair, for example, SEQ ID NO:4 and SEQ ID NO:5, under conditions suitable for amplification, wherein an amplification product, if any, generated by the methylation-specific amplification primer pair has a first length, and wherein an amplification product, if any, generated by the unmethylation-specific amplification primer pair has a second length, which is different from the first length, whereby generation of an amplification product having the first length is indicative methylation of cytosine residues in CpG dinucleotides in the SOCS-1 gene of the test cell, thereby identifying the test cell as a neoplastic cell.

The present invention also relates to a method of reducing or inhibiting unregulated growth of a cell exhibiting methylation silenced transcription of a SOCS/CIS gene. Such a method can be performed by providing the cell exhibiting unregulated growth with a polypeptide encoded by the methylation-silenced SOCS/CIS gene, for example, by restoring expression of the SOCS/CIS gene in the cell.

In one embodiment, restoring expression of the SOCS/CIS polypeptide comprises contacting the cell with a demethylating agent such as 5-aza-2'-deoxycytidine. Such contacting can be performed on a cell in culture by adding the demethylating agent to the cell culture medium. Such a cell in culture can be a cell of an established cell line, or can be a cell, generally a population of cells, which can be a mixed population of cells, that has been removed from a subject and is being contacted ex vivo, for example, to determine whether contact with the particular demethylating agent can restore the SOCS/CIS gene expression, or to restore such SOCS/CIS gene expression, after which the cells, which can be, for example, bone marrow cells of an individual suffering from multiple myeloma or an acute leukemia, are administered back into the subject. Contacting the cell with the demethylating agent also can be performed in vivo by administering the agent to a subject. Where convenient, the demethylating agent is administered at or near the site of the cells exhibiting unregulated growth in the subject, or into a blood vessel in which the blood is flowing to the site of the target cells.

In another embodiment, restoring expression of the SOCS/CIS polypeptide to a cell exhibiting unregulated growth is performed by introducing a polynucleotide encoding the SOCS/CIS polypeptide into the cell, whereby the SOCS/CIS polypeptide is expressed from the polynucleotide. For example, where the cell is characterized by methylation-silenced transcription of the SOCS-1 gene, the polynucleotide can comprise SEQ ID NO:1. The polynucleotide encoding the SOCS/CIS polypeptide can include, in addition to SOCS/CIS polypeptide coding sequence, operatively linked transcriptional regulatory elements, translational regulatory elements, and the like, which allow for expression of the encoded polypeptide at least in the target cell. The polynucleotide can be introduced into a cell in culture, for example, a cell ex vivo, or can be introduced into a cell in vivo. In addition, the polynucleotide can be in the form of a naked DNA molecule, or can be formulated in a matrix that facilitates entry of the polynucleotide into the particular cell, for example, a liposome, in which case the polynucleotide contains the required operatively linked regulatory elements. The SOCS/CIS polynucleotide also can be contained in a vector, which can provide some or all of the regulatory elements required for expression of the encoded SOCS/CIS polypeptide. The vector can be any vector suitable for introducing a polynucleotide into the particular cell exhibiting unregulated growth, including, for example, a viral vector such as a viral vector derived from a retrovirus or other lentivirus, an adenovirus, an adeno-associated virus, or a herpesvirus.

In still another embodiment, the SOCS/CIS polypeptide is provided directly to the cell exhibiting unregulated growth. The polypeptide can be contacted with the cell in vitro under conditions that result in sufficient permeability of the cell such that the polypeptide can cross the cell membrane, or the polypeptide can be microinjected into the cells. Where the SOCS/CIS polypeptide is contacted with a cell in situ in an organism, it can comprise a fusion protein, which includes, for example, a peptide or polypeptide component that facilitates transport across the cell membrane (e.g., a human immunodeficiency virus (HIV) TAT protein transduction domain), or can be formulated in a matrix that facilitates entry of the polypeptide into a cell.

The present invention also relates to a method for treating a cancer patient, wherein cancer cells in the patient exhibit methylation silenced SOCS-1 gene expression, by providing SOCS-1 polypeptide (SEQ ID NO:20) to the cancer cells, thereby inducing apoptosis of the cells. SOCS-1 polypeptide can be provided to the cells by contacting the cells with a demethylating agent, for example, by administering the demethylating agent to the subject in an amount sufficient to restore SOCS-1 gene expression in the cancer cells, or by introducing a polynucleotide encoding SOCS-1, for example, the polynucleotide set forth as SEQ ID NO:1 or a polynucleotide encoding SEQ ID NO:20, into the cancer cells under conditions sufficient for expression of the encoded SOCS-1 polypeptide in the cancer cells. Where the polynucleotide is administered to a subject, the polynucleotide can be contained in a vector, particularly a vector derived from a virus that preferentially infects the cells from which the cancer cells arose, for example, a vector derived from a hepatitis vector where the cancer cells are hepatocellular carcinoma cells, or a vector derived from HIV where the cancer cells are T cell leukemia cells. The polynucleotide, which can be contained in a vector, also can be formulated with a matrix such as a liposome, which can be further modified to contain a receptor (or ligand) on its surface, wherein the receptor (or ligand) can specifically bind a cognate ligand (or receptor) expressed by the cancer cells, for example, the liposome can contain on its surface antibodies such as anti-idiotype antibodies that specifically bind with antibodies expressed by plasma cells associated with a multiple myeloma. The polynucleotide also can comprise an operatively linked regulatory element that directs expression of the polynucleotide, particularly in a tissue specific manner such that the polynucleotide is expressed only in the target cells, for example, an I-fetoprotein promoter, which is active in hepatocytes, including hepatocellular carcinoma cells; or a leukosialin (CD43) or leukocyte common antigen (LCA; CD45) promoter, which is active in leukocytes or hematopoietic cells, respectively.

The present invention further relates to a method for selecting a therapeutic strategy for treating a cancer patient by detecting methylation-silenced transcription of a SOCS/CIS gene in cancer cells of the patient. Such a method can be performed by examining a sample suspected of containing cancer cells from the patient for decreased expression of a SOCS/CIS gene product due to methylation-silenced transcription, whereby detecting decreased expression of a SOCS/CIS gene product indicates selecting an agent that restores the SOCS/CIS gene product to the cancer cells as a component of the therapeutic strategy.

Upon determining that a cancer is associated with methylation-silenced transcription of a SOCS/CIS gene, the agent selected for restoring SOCS/CIS gene product to the cell can be an agent such as a demethylating agent, which restores transcriptional activity of the silenced SOCS/CIS gene, or an agent that modulates the activity of an effector molecule downstream of the SOCS/CIS gene in a signal transduction pathway, for example, an agent such as AG490, which inhibits the activity of JAK2 kinase, which is downstream of and regulated by SOCS-1 in a signal transduction pathway. The agent to be selected also can be selected based on the particular SOCS/CIS gene that is methylation-silenced. For example, where the cancer is associated with methylation-silenced SOCS-1 gene expression, the agent can be the SOCS-1 protein, or a polynucleotide encoding SOCS-1, such as the polynucleotide set forth in SEQ ID NO:1, or a substantially similar polynucleotide having, for example, one or more silent nucleotide changes that change a codon to a degenerate codon encoding the same amino acid.

The present invention also relates to a method of treating a subject suffering from hepatocellular carcinoma (HCC) or multiple myeloma (MM), wherein cells associated with the HCC or MM exhibit methylation silenced SOCS-1 gene expression, the method comprising administering an amount of AG490 to the subject sufficient to induce apoptosis of the cells associated with the cancer.

The present invention further relates to an isolated oligonucleotide, which is useful as a probe or a primer for detecting a SOCS-1 gene sequence, or in combination as amplification primer pairs for amplifying all or a portion of a SOCS-1 gene sequence, including, for example, a methylated SOCS-1 gene sequence or an unmethylated SOCS-1 gene sequence. For example, the present invention provides an oligonucleotide selected from any one of SEQ ID NOS:2 to 6 and 12 to 17, and further provides a plurality of such oligonucleotides, which includes at least two of the oligonucleotides set forth as SEQ ID NOS:2 to 6 and 12 to 17. Also provided is an amplification primer pair, comprising a forward primer and a reverse primer such as those set forth as SEQ ID NO:2 and SEQ ID NO:3; SEQ ID NO: 4 and SEQ ID NO:5; SEQ ID NO:6 and SEQ ID NO:7; SEQ ID NO:12 and SEQ ID NO:13; SEQ ID NO:14 and SEQ ID NO:15; or SEQ ID NO:16 and SEQ ID NO:17; as well as a plurality of such amplification primer pairs, comprising at least two primer pairs, including at least one of the primer pairs set forth as SEQ ID NO:2 and SEQ ID NO:3; SEQ ID NO: 4 and SEQ ID NO:5; SEQ ID NO:6 and SEQ ID NO:7; SEQ ID NO:12 and SEQ ID NO:13; SEQ ID NO:14 and SEQ ID NO:15; or SEQ ID NO:16 and SEQ ID NO:17.

In one embodiment, the amplification primer pair, or a plurality thereof, includes SEQ ID NO:2 and SEQ ID NO:3, which can specifically amplify a methylated SOCS-1 gene sequence. In another embodiment, the amplification primer pair, or a plurality thereof, includes SEQ ID NO:4 and SEQ ID NO:5, which can specifically amplify a unmethylated SOCS-1 gene sequence. In still another embodiment, a plurality of primer pairs, which includes SEQ ID NOS:2 and 3, and SEQ ID NOS:4 and 5 is provided.

The present invention further relates to a kit, which contains reagents useful for practicing a method of the invention. As such, a kit of the invention can contain, for example, an isolated oligonucleotide, comprising any one of SEQ ID NOS:2 to 6 and 12 to 17; at least two isolated oligonucleotides selected from SEQ ID NOS:2 to 6 and 12 to 17; at least one amplification primer pair selected SEQ ID NO:2 and SEQ ID NO:3; SEQ ID NO: 4 and SEQ ID NO:5; SEQ ID NO:6 and SEQ ID NO:7; SEQ ID NO:12 and SEQ ID NO:13; SEQ ID NO:14 and SEQ ID NO:15; and SEQ ID NO:16 and SEQ ID NO:17; an amplification primer pair comprising SEQ ID NO:2 and SEQ ID NO:3; or an amplification primer pair comprising SEQ ID NO:4 and SEQ ID NO:5.

In one embodiment, a kit of the invention contains a plurality of oligonucleotides, including those having sequences as set forth in SEQ ID NO:2, SEQ ID NO:3, SEQ ID NO:4, and SEQ ID NO:5, wherein the oligonucleotides are useful as probes, or in combination as amplification primer pairs, for detecting methylated SOCS-1 gene sequences, unmethylated SOCS-1 gene sequences, or both. In another embodiment, a kit of the invention contains an amplification primer pair, or a plurality thereof, wherein at least one oligonucleotide of the primer pair is selected from SEQ ID NOS:2 to 6 and 12 to 17. A kit of the invention can further include one or more amplification primer pairs selected to allow nested amplification of an amplification product generated using a first amplification primer pair of the kit. A kit of the invention also can contain reagents for performing an amplification reaction; a reagent that modifies methylated cytosine residues; a methylation sensitive restriction endonuclease; or a combination of such reagents.

DETAILED DESCRIPTION OF THE INVENTION

As disclosed herein unregulated cell growth as occurs in various cancers has been correlated with methylation-silenced transcription of a suppressor of cytokine signaling (SOCS)/cytokine-inducible SH2 protein (CIS) family member (SOCS/CIS) gene. The correlation of methylation-silenced SOCS/CIS gene expression and cancer is exemplified by the demonstration that methylation-silenced transcription of the SOCS-1 gene is associated with various types of cancer, including hepatocellular carcinoma, multiple myeloma, and acute leukemias, and that restoration of SOCS-1 gene expression is such cancer cells results in apoptosis of the cells. As such, the present invention provides methods of diagnosing a cancer by detecting methylation-silenced transcription of a SOCS/CIS gene, as well as methods of treating such cancers by restoring the SOCS/CIS gene product to the cells.

The SOCS/CIS family of proteins has been implicated in the negative regulation of several cytokine pathways, including, for example, interleukin-6 (IL-6). SOCS-1 specifically associates with Janus kinase (JAK) to switch off cytokine signaling via the JAK/signal transducer and activator of transcription (STAT) pathways of transcriptional activation (Masuhara et al., *Biophys. Res. Comm.* 239:439-446, 1997; Hilton et al., *Proc. Natl. Acad. Sci. USA* 95:114-119, 1998; Starr et al., *Nature* 387:917-921, 1997, each of which is incorporated herein by reference). As disclosed herein, aberrant methylation in the CpG island of the SOCS-1 gene correlated with transcriptional silencing of SOCS-1 in hepatocellular carcinoma (HCC) cell lines, including an incidence of aberrant methylation of 65% in 26 human primary HCC tumor samples analyzed (Example 1; see, also, Yoshikawa et al., *Nat. Genet.* 28:29-35, 2001, which is incorporated herein by reference). In HCC cells exhibiting methylation-silenced SOCS-1 gene expression, restoration of SOCS-1 gene expression suppressed the growth rate and anchorage-independent growth of the cells, and suppressed constitutively activated JAK2 expression. Moreover, the growth suppression was due to apoptosis of the cells, and was reproduced by treatment of the cells AG490, a specific chemical inhibitor of JAK2 that reversed constitutive phosphorylation of STAT3 in SOCS-1 inactivated cells.

In view of the results observed for HCC cell lines and primary HCC tumor samples, and further in view of role of IL-6 as a survival factor in multiple myeloma (MM), methylation of the SOCS-1 gene CpG island was examined in MM cell lines and in primary MM samples. Aberrant SOCS-1 methylation was detected in two IL-6-dependent MM cell lines, U266 and XG1, and, as for HCC cells, correlated with transcriptional silencing. Treatment of the MM cells with a demethylating agent, 5-aza-2'-deoxycytidine (5-azacytidine), resulted in up-regulation of SOCS-1 gene expression. Methylation-silenced transcription of SOCS-1 in the MM cell lines correlated with greater sensitivity to the chemical JAK inhibitor, AG490. Using methylation-specific PCR (MSP), SOCS-1 hypermethylation was detected in 62.9% (23/35) of MM patient samples. In comparison, analysis of malignant lymphomas of various histologic types revealed that SOCS-1 was hypermethylated in only 3.2% (2/62), and no methylation of the SOCS-1 gene was detected in normal peripheral blood leukocytes or bone marrow cells.

Since the JAK/STAT pathway has a crucial role in hematological cells, and is negatively regulated by SOCS-1, the methylation status of the SOCS-1 gene CpG island also was examined with respect to acute leukemias. SOCS-1 gene methylation was detected in each of the types of acute leukemia examined, including in samples from a de novo acute myelogenous leukemia (AML), a secondary AML transformed from myelodysplastic syndrome (MDS), a B cell acute lymphocytic leukemia (ALL), and a T cell ALL. The incidence of methylation was 31% for all of the samples examined, and was 50% for the MDS based AML. Constitutive activation of STAT1, STAT3 and STAT5 was detected in an AML cell line, and treatment with AG490 induced apoptosis, and resulted in decreased STAT1 and STAT3 tyrosine phosphorylation levels.

These results demonstrate that inactivation of SOCS-1 gene expression due to hypermethylation of the SOCS-1 gene correlated to the unregulated growth characteristic of several different types of cancer, including hepatocellular carcinoma, multiple myeloma, and acute leukemia. In addition, the results disclosed herein demonstrate that agents such as the demethylating agent, 5-azacytidine, which restores SOCS-1 gene expression in cancer cells, and the JAK inhibitor, AG490, which circumvents the lack of SOCS-1 activity, can induce apoptosis of the cancer cells. The high prevalence of the aberrant SOCS-1 methylation, and its growth suppression activity, demonstrates the importance of the constitutive activation of the JAK/STAT pathway in various cancers, and indicates that SOCS-1 methylation status can be targeted for diagnostic and therapeutic strategies. Accordingly, the present invention provides methods for diagnosis of a cancer associated with aberrant CpG methylation in the SOCS-1 gene, methods for treating such cancers, and reagents for practicing such methods.

SOCS-1 is a member of the SOCS/cytokine-inducible SH2 protein (CIS) family of proteins (SOCS/CIS family). The SOCS/CIS family members have a poorly conserved N-terminal region, a central SH2 domain, which can interact with phosphorylated tyrosine, and a SOCS box, which is a domain that is conserved among at least 20 proteins but for which a function has not yet been described (Endo et al., *Nature* 387:921-924, 1997; Naka et al., *Nature* 387:924-929, 1997). SOCS-1 is involved in a negative feedback loop of cytokine signaling (see, for example, Masuhara et al., supra, 1997; Hilton et al., supra, 1998; Starr et al., supra, 1997). The human SOCS-1 gene is localized in chromosome 16p13.3, just downstream of the protamine gene cluster, and contains a single exon gene encoding the 211 amino acid residue SOCS-1 protein (see, for example, Kramer et al., *J. Exp. Zool.* 282:245-255, 1998, which is incorporated herein by reference; see, also, SEQ ID NO: 20). The SOCS-1 gene lies within a large CpG island spanning about 2.5 kilobases (kb).

SOCS-1 expression renders cells unresponsive to IL-6 stimulation. Various cytokines, including, for example, IL-4, IL-13, interferon-γ (IFN-γ), leukemia inhibitory factor (LIF), and granulocyte-monocyte colony stimulating factor (GM-CSF), as well as IL-6, can induce SOCS-1 gene expression in hematologic cells; SOCS-1 interacts specifically with JAK to turn off the cytokine-mediated signal transduction. For example, the SH2 domain of SOCS-1 can specifically bind to a JH1 domain of JAK2, inhibiting the phosphorylation of JAK2 and down-regulating the JAK/STAT pathway (see Hilton et al., supra, 1998). SOCS-1 also inhibits the biological effects of cytokines in vivo such that forced SOCS-1 expression interrupts macrophage differentiation induced by IL-6, and suppresses CD23 expression induced by IL-4 (see Losman et al., *J. Immunol.* 162:3770-3774, 1999). As disclosed herein, SOCS-1 expression also has a role in the loss of growth control characteristic of cancer.

Relationships between protein tyrosine phosphorylation and cancer have been demonstrated (see, for example, Ihle et al., *Nature*, 377:591-594, 1995). For example, over-expression of a phosphotyrosine protein phosphatase in NIH/3T3 cells and in v-erbB transformed cells inhibited the growth of both cell types in culture (Rampone it al., *Int. J. Cancer* 51:652-656, 1992). PTEN is an example of a protein tyrosine phosphatase that is mutated in various types of cancer, and reconstruction of the PTEN gene in the mutant cell lines resulted in significant growth suppression (Furnari et al., Proc. Natl. Acad. Sci. USA 94:12,479-12,484, 1997). Mice that were homozygous for mutations in the "motheaten" gene that result in defective hematopoietic cell phosphatase showed CSF-1 independent proliferation of macrophage, and mice that were heterozygous mutants showed an increased incidence of lymphoreticular neoplasia. A mutation in the EPOR gene resulted in expression of mutant protein that hematopoietic cell phosphatase was unable to bind, resulting in induced prolonged activation of JAK2 (Klingmuller et al., *Cell* 80:729-738, 1995).

Abnormalities of the JAK/STAT pathway have been associated with cancer (Ihle et al., supra, 1995; Garcia et al., *Cell Growth Diff* 8:1267-1276, 1998). For example, a dominant gain-of-function mutation in a *Drosophila* JAK (hop$^{tum-1}$), in which the *Drosophila* JAK protein was phosphorylated to a greater extent than in the wild type, caused leukemia-like abnormalities (Luo et al., *EMBO J.* 14:1412-1420, 1995; Harrison et al., *EMBO J.* 14:2857-2865, 1995). In addition, a structurally abnormal JAK was detected in human cancers. For example, a t(9; 12)(p24; p13) chromosomal translocation was found in T cell childhood ALL, resulting in a fusion of the catalytic domain of the JAK2 to an oligomerization domain of ETV6 and constitutive activation of its tyrosine kinase activity (Lacronique et al., *Science* 278:1309-1312, 1997). Furthermore, a SH2 domain mutant of STAT3 can spontaneously form homodimers and bind DNA, resulting in transcriptional activation, and immortalized mouse fibroblasts transfected with the mutant STAT3 acquired the ability to grow in soft agar and were tumorigenic in nude mice (Bromberg et al., *Cell* 98:295-303, 1999). In contrast, expression of a STAT3 dominant-negative induced apoptosis in myeloma cells (Catlett-Facone et al., *Immunity* 10:105-115, 1999).

In addition to inducing SOCS-1 gene expression, IL-6 also plays an important role in B cell growth and differentiation into plasma cells, and is the essential growth and survival factor for neoplastic cells in the pathogenesis of multiple myeloma (Klein et al., *Blood* 85:863-872, 1995; Hallek et al., *Blood* 91:3-21. 1998; Hirano et al., *Oncogene* 19:2548-2556, 2000). IL-6 binds to a specific membrane receptor (IL-6R), and the IL-6/IL-6R complex induces the dimerization of the receptor subunit gp 130. Subsequently, members of the JAK family, which cross-phosphorylate each other and the cytoplasmic domains of the receptors on tyrosine residues, become activated, thus providing docking sites for latent STAT transcription factors, which, in turn, become phosphorylated and dimerize before entering the nucleus and initiating transcription of target genes, including proliferative genes such as c-myc an cyclin D1, and anti-apoptotic genes such as pim-1 and bc1-x1 (see, for example, Heinrich et al., *Biochem. J.* 334:297-314, 1998; Imada et al., *Mol. Immunol.* 37:1-11, 2000). Under physiological conditions, this signaling is quickly attenuated, and the stimulation by the cytokine is thereby limited. A key component of this negative feedback loop is SOCS-1, which down-regulates JAK/STAT effects by directly interacting with JAK.

There is increasing evidence for a role of the JAK/STAT pathway in the pathogenesis of different leukemias. Constitutive activation of several STAT proteins, particularly STAT1, STAT3 and STAT5 has been found in different types of leukemia (see, for example, Coffer et al., *Oncogene*, 19:2511-2522, 2000; Ward et al., *Blood* 95:19-29, 2000; Lin et al., *Oncogene* 19:2496-2504, 2000). For example, STAT3 (28%) and STAT5 (22%) are activated in AML (Xia et al., *Cancer Res.* 58:3173-3180, 1998). In addition, a number of defined genetic aberrations have been shown to be responsible for activation of the JAK/STAT pathway, including the t(9; 12)(p24; p13) chromosomal translocation as discussed above (Lacronique et al., supra, 1997).

SOCS family proteins function as negative regulators of JAK/STAT signaling. Eight members of the SOCS family have been identified, including SOCS-1 to SOCS-7 and CIS (cytokine-inducible SH2-containing protein; Alexander et al., *J. Leuk. Biol.* 66:588-592, 1999; Nicola et al., *Expt. Hematol.* 28:1105-1112, 2000). Blocking of JAK activation by SOCS-1 results in inhibition of the JAK/STAT signal transduction pathway, thus suppressing signaling by a wide variety of factors including, for example, IL-6, IL-4, LIF, oncostatin M, growth hormone, prolactin, thrombopoietin and interferons (see Greenhalgh and Hilton, *J. Leuk. Biol.* 70:348-356, 2001). As disclosed herein, methylation of the SOCS-1 gene results in transcriptional silencing of SOCS-1 gene expression, thus leading to unregulated JAK/STAT signal transduction activity in cancer cells, and unregulated growth of the cells (see Examples 1 to 3).

The silencing of gene transcription associated with aberrant DNA methylation of CpG dinucleotides in normally unmethylated gene promoter regions is the most widely studied epigenetic abnormality in tumorigenesis. The binding of protein complexes consisting of methyl-CpG-binding domains, transcriptional co-repressors, chromatin remodeling proteins and histone deacetylases to hypermethylated DNA regions results in a transcriptionally repressed (silenced) chromatin state. In eukaryotic cells, methylation of cytosine residues that are immediately 5' to a guanosine residue occurs predominantly in CG poor regions. In contrast, CpG islands generally remain unmethylated in normal cells, except during X chromosome inactivation and parental specific imprinting, where methylation of 5' regulatory regions is associated with transcriptional repression. De novo methylation of the retinoblastoma (Rb) gene has been demonstrated in a small fraction of retinoblastomas (Sakai et al., *Am. J. Hum. Genet.* 48:880, 1991), and aberrant methylation of the VHL gene was found in a subset of sporadic renal cell carcinomas (Herman et al., *Proc. Natl. Acad. Sci. USA* 91:9700-9704, 1994). Expression of a tumor suppressor gene can also be abolished by de novo DNA methylation of a normally unmethylated 5'CpG island (see, for example, Issa et al., *Nature Genet.* 7:536, 1994; Merlo et al., *Nature Med.* 1:686, 1995; Herman et al., *Cancer Res.* 56:722, 1996).

Aberrant methylation of promoter regions in CpG islands also has been associated with the development of cancer. In hematopoietic malignancies, for example, hypermethylation of E-cadherin (Graff et al., *Cancer Res.* 55:5195-5199, 1995), DAP-kinase (Katzenellenbogen et al., *Blood* 93:4347-4353, 1999), and the cell cycle regulators p15$^{INK4B}$ and p16$^{INK4A}$, is associated with gene inactivation (Herman et al., *Cancer Res.* 57:837-841 1997; Melki et al., *Blood* 95:3208-3213, 2000; Ng et al., *Clin. Canc. Res.* 7:1724-1729, 2001). Transcriptional silencing due to hypermethylation also has been detected in the CDKN2A gene (Herman et al., *Cancer Res.* 55:4525-4530, 1995), MGMT (Esteller et al., *Cancer Res.* 59:793-797, 1999), and MLH1 gene (Herman et al., *Proc. Natl. Acad. Sci. USA* 95:6870-6875, 1998).

Hypermethylation of a CpG island at chromosome position 17p13.3 has been observed in multiple common types of human cancers (Makos et al., *Proc. Natl. Acad. Sci. USA* 89:1929, 1992; Makos et al., *Cancer Res.* 53:2715, 1993; Makos et al., *Cancer Res.* 53:2719, 1993), and coincides with timing and frequency of 17p loss and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes (Baylin et al., *Cancer Cells* 3:383, 1991; Jones and Buckley, *Adv. Cancer Res.* 54:1-23, 1990). This change also has been associated with the loss of expression of VHL, a renal cancer tumor suppressor gene on 3p (Herman et al., supra, 1994), the estrogen receptor gene on 6q (Ottaviano et al., *Cancer Res.* 54:2552, 1994), and the H19 gene on 11p (Steenman et al., *Nature* Genetics, 7:433, 1994).

A DNA region, termed Spot7, demonstrated the highest aberration incidence of up to 88% in restriction landmark genomic scanning (RLGS) analysis of HCC (Nagai et al., *Cancer Res.* 54:1545-1550, 1994). Spot7 was localized to chromosome 16, where the aberrant DNA in the RLGS analysis was most concentrated (Yoshikawa et al., *Gene* 197:129-135, 1997). As disclosed herein, a Not I restriction endonuclease site in the SOCS-1 gene in the Spot7 region was methylated in HCC, and further examination revealed that methylation silencing of the SOCS-1 gene, and loss of growth suppression activity by SOCS-1 protein, correlated with HCC, as well as other cancers, including acute leukemias and multiple myeloma.

Accordingly, the present invention provides a method for identifying a cell that exhibits, or is predisposed to exhibiting, unregulated growth, by detecting methylation of cytosine residues in CpG dinucleotides in a CpG island of a SOCS/CIS gene in a test cell, or an extract comprising nucleic acid molecules of the test cell, wherein the SOCS/CIS gene methylation results in a reduced level of transcription of the gene in the test cell as compared to a corresponding cell that exhibits normal regulated growth. As used herein, the term "methylation" or "hypermethylation", when used in reference to a SOCS/CIS gene, means that cytosine residues of CpG dinucleotides in a CpG island associated with the gene are methylated at the 5'-position, i.e., 5'-methylcytosine. The terms are used interchangeably because the cytosine residues in a SOCS/CIS gene CpG island normally are unmethylated, and, therefore, any amount of cytosine methylation in a CpG island also can be considered hypermethylation.

A CpG island of SOCS/CIS gene is exemplified by the CpG island that spans about 2.5 kilobases of chromosome 16, including the SOCS-1 gene, and further spanning about nucleotides 200 to 500 of the SOCS-1 coding sequence beginning with the ATG start codon (see SEQ ID NO:1). The term "methylation status" is used herein to refer to relative abundance, including the presence or absence, of methylated cytosine residues of CpG dinucleotides in a CpG island. As such, a method of the invention provides a means to determine the methylation status of a SOCS/CIS gene in a cell.

In general, the cytosine residues in a CpG island are not methylated in a transcriptionally active SOCS/CIS gene and, therefore, the detection of methylated cytosine residues in a CpG island indicates that the SOCS/CIS gene is not being expressed. As such, reference herein to a "methylation-silenced" SOCS/CIS gene means that the gene is not being transcribed, or is being transcribed at a level that is decreased with respect to the level of transcription of a corresponding unmethylated SOCS/CIS gene. Methylation-silencing is detectable by progressively decreasing levels of transcriptional activity of a gene such as SOCS-1 as methylation of cytosine residues in CpG dinucleotides of a CpG island increases to encompass about 15% to 20% of the cytosine residues, at which point transcription generally is completely silenced. A consequence of methylation-silenced SOCS/CIS gene expression is that a cell containing the gene has reduced levels of, or completely lacks, the SOCS/CIS gene product such that a regulatory activity due to the SOCS/CIS gene product in the cell is reduced or absent. For example, methylation-silenced SOCS-1 gene expression in a cell results in constitutive activation of the JAK2 kinase and, therefore, unregulated growth of the cell, due to an insufficient amount of SOCS-1 protein in the cell to down-regulate JAK2 activity.

A method of the invention requires, in part, a comparison of SOCS/CIS gene CpG island methylation in a test cell or sample with the level of methylation, if any, of a corresponding SOCS/CIS gene in a corresponding cell exhibiting regulated growth. As used herein, the term "corresponding" means a reference material, with which a test material is being compared. Generally, the reference material provides a control or standard with which the test material is compared. For example, reference to a corresponding unmethylated SOCS/CIS gene, with respect to a SOCS/CIS gene being examined for methylation status, means that the unmethylated SOCS/CIS gene is the same type of gene as the SOCS/CIS gene being examined for methylation status, e.g., the test gene and the corresponding unmethylated gene are both human SOCS-1 genes, or are both murine CISH genes, etc. Reference to a corresponding cell exhibiting regulated growth, with respect to a test cell, generally refers to a normal cell, i.e., a cell that has a cell cycle and growth pattern characteristic of a population of such cells in a healthy individual, for example, a normal hepatocyte, where the test cell is suspected of being a HCC cell, or a normal B cell, where the test cell is suspected of being a B cell leukemia cell. Generally, a cell that exhibits regulated growth survives for a period of time, after which apoptosis is induced resulting in programmed death of the cell.

In general, a corresponding SOCS/CIS gene or a corresponding cell exhibiting regulated growth will be known to those in the art. For example, it will be recognized that a particular SOCS/CIS gene in a particular cell type such as a SOCS-1 gene in a hepatocyte will have a level and/or pattern of methylation, if any, that is characteristic for that gene in the particular cell type, and that such methylation status can be determined by examining the SOCS/CIS gene sequence, using methods as disclosed herein, in a statistically significant number of hepatocytes from individuals of believed to be normal and healthy representatives of a population. Similarly, the growth characteristics of a statistically significant number of cells from a healthy individual or from individuals of a population can be examined to determine the parameters of normal regulated cell growth for the particular cell type. Such parameters can include, for example, the ability to grow (or not grow) in soft agar, the susceptibility of the cells to contact inhibition of growth, the number of divisions the cells can undergo under defined conditions in a tissue culture medium, and the responsiveness of the cells to a growth factor, hormone, or the like.

A method of the invention provides a means to identify a cell that exhibits, or is predisposed to exhibiting unregulated growth. As used herein, reference to a "cell exhibiting unregulated growth" means a cell that has a growth characteristic that is different from that of a corresponding cell that exhibits regulated growth. Reference to a "cell predisposed to exhibiting unregulated growth" means a cell that appears to have the same growth characteristics in situ as that of a corresponding cell in situ, but that exhibits unregulated growth when examined under appropriate conditions, for example, in a soft agar assay, wherein the cell grows, or in a monolayer assay, wherein the cell does not exhibit contact inhibition of growth. Such cells can be identified by detecting methylation-silenced SOCS/CIS gene expression according to a method of the invention.

The cell exhibiting, or predisposed to exhibiting, unregulated growth generally, but not necessarily, is a neoplastic cell, which can be a premalignant cell having a low level of CpG island methylation (e.g., about 5% to 10%) and, therefore, a reduced level of expression of a SOCS/CIS gene product, or a malignant cell, i.e., a cancer cell, in which about 20% or more of the cytosine residues in the CpG island are methylated and, therefore, transcription is completely inhibited. Such cells, which exhibit methylation-silenced SOCS/CIS gene expression, are exemplified herein by hepatocellular carcinoma cells, multiple myeloma cells, and various types of acute leukemia cells, each of which exhibit methylation-silenced SOCS-1 gene expression. In addition, such cells can include ovarian carcinoma cells, breast carcinoma cells, pancreatic cancer cells, glioblastoma cells, lung cancer cells, melanoma cells, and the like.

A method of the invention is practiced using a sample comprising a test cell, or an extract of the test cell that includes nucleic acid molecules of the cell, particularly genomic DNA, including all or a portion comprising the CpG island of a SOCS/CIS gene that is to be examined for methylation status. Generally, the test cell is a cell that is suspected of being a cell that exhibits unregulated growth, for example, a biopsy sample of suspicious lesion, or is a cell that is (or was) in proximity to a premalignant or malignant cell, for example, cell samples taken at one or few places outside of the region of a suspicious lesion, such test cell providing an indication, for example, of the extent to which a surgical procedure should be performed, or a cell sample taken from a surgical margin, such test cells being useful for determining whether a cancer has been completely removed, or for determining whether a cancer has recurred.

A test cell examined according to a method of the invention also can be a primary cell that has been obtained from a subject and placed in culture, for example, for the purpose of establishing a primary cell culture that exhibits substantially the same growth characteristics as the cells from which the culture was established, or for the purpose of treating and/or expanding the cells for readministration to the subject. For example, bone marrow cells can be obtained from a cancer patient suffering from multiple myeloma or from an acute leukemia, wherein the cells exhibit methylation-silenced SOCS/CIS gene expression. The cells be treated in culture using an agent that restores the SOCS/CIS gene expression (see below), optionally can be expanded in culture, then can be administered back to the subject.

A test cell can be obtained from a subject in any way typically used in clinical setting for obtaining a sample containing the cells. For example, the test cells (or a sample comprising the test cells) can be obtained by a biopsy procedure such as needle biopsy of an organ or tissue containing the cells to be tested. As such, the test cells can be obtained from a liver sample, a bone marrow sample, a skin sample, a lymph node sample, a kidney sample, a lung sample, a muscle sample, a bone sample, a brain sample, or the like. The test cell also can be a component of a biological fluid, for example, blood, lymph, cerebrospinal fluid, saliva, sputum, stool, urine, or ejaculate. If appropriate, the test cells also can be obtained by lavage, for example, for obtaining test cells from uterus, the abdominal cavity, or the like, or using an aspiration procedure, for example, for obtaining a bone marrow sample.

A method of the invention also can be practiced using an extract of a test cell, wherein the extract includes nucleic acid molecules of the test cell, particularly genomic DNA, including all or a CpG island containing portion of a SOCS/CIS gene to be examined. The extract can be a crude extract comprising, for example, a freeze-thawed sample of a tissue containing the test cells; can comprise partially purified genomic DNA, which can include, for example, components of the nuclear matrix; or can comprise substantially purified genomic DNA, which is obtained, for example, following treatment with a protease and alcohol precipitation. In certain embodiments, the test cell also can be a component of a histologic sample that is embedded in paraffin.

Methylation of a CpG dinucleotide in a CpG island of a SOCS/CIS gene can be detected using any of various well known methods for detecting CpG methylation of a nucleic acid molecule. Such methods include contacting the SOCS/CIS gene sequence with one or a series of chemical reagents that selectively modify either unmethylated cytosine residues or methylated cytosine residues, but not both, such that the presence or absence of the modification can be detected; contacting the SOCS/CIS gene sequence with a methylation sensitive restriction endonuclease, which has a recognition site that includes a CpG dinucleotide, and that cleaves a recognition site either having a methylated cytosine residue of the CpG or lacking a methylated cytosine residue of the CpG, but not both, such that the presence or absence of cleavage of the sequence can be detected; or contacting the SOCS/CIS gene sequence with an oligonucleotide probe, primer, or amplification primer pair that specifically hybridizes to the SOCS/CIS gene sequence and allows a determination to made as to whether the CpG methylation is present. Examples of such methods are provided herein, and modifications and variations on such methods are well known in the art.

In one embodiment, methylation of CpG dinucleotides in a CpG island of a SOCS/CIS gene sequence can be detected by contacting a nucleic acid molecule, which includes all or a portion of a CpG island of the SOCS/CIS gene sequence, with a methylation sensitive restriction endonuclease for which the SOCS/CIS gene contains the restriction endonuclease recognition site. The methylation sensitive restriction endonuclease can be one that cleaves a recognition site containing a methylated cytosine residue of a CpG dinucleotide, for example, a restriction endonuclease such as Acc III, Ban I, BstN I, Msp I, or Xma I, whereby cleavage of the nucleic acid molecule indicates that SOCS/CIS gene in the test cell is methylated. Alternatively, the methylation sensitive restriction endonuclease can be one that cleaves a recognition site containing a CpG dinucleotide only when the cytosine residue of the CpG dinucleotide is unmethylated, for example, a restriction endonuclease such as Acc II, Ava I, BssH II, BstU I, Hpa II, or Not I, whereby a lack of cleavage of the nucleic acid molecule indicates that SOCS/CIS gene in the test cell is methylated.

The presence or absence of cleavage of the SOCS/CIS gene sequence by the methylation sensitive restriction endonuclease can be identified using any method useful for detecting the length or continuity of a polynucleotide sequence. For example, cleavage of the SOCS/CIS gene can be detected by Southern blot analysis, which allows mapping of the cleavage site, or using any other electrophoretic method or chromatographic method that separates nucleic acid molecules on the basis of relative size, charge, or a combination thereof. Cleavage of a SOCS/CIS gene also can be detected using an oligonucleotide ligation assay, wherein, following contact with the restriction endonuclease, a first oligonucleotide that selectively hybridizes upstream of and adjacent to a restriction endonuclease cleavage site and a second oligonucleotide that selectively hybridizes downstream of and adjacent to the cleavage site are contacted with the SOCS/CIS gene sequence, and further contacted with a ligase such that, in the absence of cleavage the oligonucleotides are adjacent to each other and can be ligated together, whereas, in the absence of cleavage, ligation does not occur. By determining the size or other relevant parameter of the oligonucleotides following the ligation reaction, ligated oligonucleotides can be distinguished from unligated oligonucleotides, thereby providing an indication of restriction endonuclease activity.

In another embodiment, methylation of a CpG dinucleotide in a CpG island of a SOCS/CIS gene is detected by contacting a nucleic acid molecule comprising the SOCS/CIS gene of the test cell with a chemical reagent that selectively modifies either an unmethylated cytosine residue or a methylated cytosine residue, and detecting a product generated due to contact with the reagent, wherein the product is indicative of the methylation status of CpG dinucleotides in the CpG island of the SOCS/CIS gene sequence. In one aspect of this embodiment, the SOCS/CIS gene sequence is contacted with hydrazine, which modifies cytosine residues, but not methylated cytosine residues, then the hydrazine treated SOCS/CIS gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated unmethylated SOCS/CIS gene sequence, gaps will be apparent at positions in the test SOCS/CIS containing methylated cytosine residues. As such, the presence of gaps is indicative of methylation of a cytosine residue in the CpG dinucleotide in the SOCS/CIS gene of the test cell.

In another aspect of this embodiment, the SOCS/CIS gene sequence is contacted with a chemical reagent comprising bisulfite ions, for example, sodium bisulfite, which converts unmethylated cytosine residues to bisulfite modified cytosine residues, then the bisulfite ion treated SOCS/CIS gene sequence is exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. As such, the sulfonate group can be removed by exposure to alkaline conditions, resulting in the formation of uracil. The DNA then can amplified, for example, by PCR, and sequenced to determine the methylation status of all CpG sites. Uracil is recognized as a thymine by Taq polymerase and, upon PCR, the resultant product contains cytosine only at the position where 5-methylcytosine was present in the starting template DNA. By comparing the amount or distribution of uracil residues in the bisulfite ion treated SOCS/CIS gene of the test cell with a similarly treated unmethylated SOCS/CIS gene sequence, detection of a decrease in the amount or distribution of uracil residues in the SOCS/CIS gene from the test cell is indicative of methylation of cytosine residues in CpG dinucleotides in the SOCS/CIS gene of the test cell. The amount or distribution of uracil residues also can be detected by contacting the bisulfite ion treated SOCS/CIS gene sequence, following exposure to alkaline conditions, with an oligonucleotide that selectively hybridizes to a SOCS/CIS gene sequence that either contains uracil residues or that lacks uracil residues, but not both, and detecting selective hybridization (or the absence thereof) of the oligonucleotide.

As used herein, the term "selective hybridization" or "selectively hybridize" refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule, including not with nucleic acid molecules encoding related but different members of a family of proteins such as member of the SOCS/CIS family of protein. Generally, an oligonucleotide useful as a probe or primer that selectively hybridizes to a target nucleic acid molecule is at least about 12 nucleotide in length, generally at least about 13 to 15 nucleotides in length, and usually at least about 18 to 20 nucleotides in length, or more. Examples of oligonucleotides useful in practicing the methods of the invention are disclosed herein as SEQ ID NOS:2 to 7 and 12 to 17, such oligonucleotides also being useful for identifying additional oligonucleotides that can selectively hybridize to other specific SOCS/CIS family member gene sequences and, therefore, be used for practicing the methods of the invention.

Conditions that allow for selective hybridization can be determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and sequence to which it is to hybridize (see, for example, Sambrook et al., "Molecular Cloning": A laboratory manual (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a target SOCS/CIS gene sequence can be detected, for example, by performing the method using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or θ-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hermanson, "Bioconjugate Techniques" (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

The amount or distribution of uracil residues in a bisulfite ion treated SOCS/CIS gene sequence following exposure to alkaline conditions also can be detected using an amplification reaction such as PCR. An amplification reaction is performed under conditions that allow selective hybridization of primers to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 primer: genomic DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes, as are well known in the art and commercially available. The amplification products can be identified as methylated or non-methylated by a sequencing method, oligomer restriction (Saiki et al., *BioTechnology* 3:1008-1012, 1985), allele-specific oligonucleotide probe analysis (Conner et al., *Proc. Natl. Acad. Sci. USA* 80:278, 1983), oligonucleotide ligation assays (Landegren et al., *Science* 241:1077, 1988), and the like (see, also, Landegren et al., *Science* 242:229-237, 1988).

In one embodiment, the amplification is performed by contacting the SOCS/CIS gene sequence with an amplification primer pair comprising a forward primer and a reverse primer under conditions suitable for amplification, wherein at least one primer of the primer pair comprises an oligonucleotide that selectively hybridizes to a SOCS/CIS gene sequence containing uracil residues, whereby generation of an amplification product is indicative of methylation of cytosine residues in CpG dinucleotides in the SOCS/CIS gene of the test cell. In another embodiment, the amplification reaction is performed by contacting the SOCS/CIS gene sequence with an amplification primer pair comprising a forward primer and a reverse primer under conditions suitable for amplification, wherein both primers of the primer pair selectively hybridize to a SOCS/CIS gene sequence containing cytosine residues, but not to a SOCS/CIS gene sequence containing uracil residues, whereby generation of an amplification product is indicative of a lack of methylation of cytosine residues in CpG dinucleotides in the SOCS/CIS gene of the test cell.

In still another embodiment, a methylation-specific amplification reaction such as methylation-specific PCR (MSP) is used alone, or in combination with bisulfite treatment, to detect the methylation status of a nucleic acid molecule (see U.S. Pat. Nos. 6,265,171; 6,200,756; and 6,017,704, each of which is incorporated herein by reference; see, also, Example 1). MSP is a particularly sensitive method that allows detection of low numbers of methylated alleles and the use of small amounts of a nucleic acid sample, including paraffin-embedded materials, and also can be conveniently adapted to a multiplex analysis, including, for example, simultaneous detection of unmethylated and methylated products in a single sample, thus providing an internal control.

The amplification primer pairs used in an MSP reaction are designed to specifically distinguish between bisulfite untreated or unmodified DNA, and methylated and unmethylated DNA. MSP primer pairs for the unmethylated DNA (unmethylation-specific primer pair) generally have a thymidine residue in the 3'-CpG pair to distinguish it from the cytosine residue retained in methylated DNA, and the complement is designed for the antisense primer. MSP primer pairs usually contain relatively few cytosine or guanine residues in the sequence because cytosine is absent in the sense (forward) primer and the guanine is absent in the antisense (reverse) primer; cytosine becomes modified to uracil, which is amplified as thymidine in the amplification product. An MSP (unmethylation-specific) primer pair is exemplified herein by the primer pair set forth as SEQ ID NOS:4 and 5, and a methylation-specific primer pair is exemplified herein by the primer pair set forth as SEQ ID NOS:2 and 3. In view of the exemplified methylation-specific and unmethylation-specific primer pairs, and of the above description for designing such primer pairs, it will be recognized that additional methylation-specific and unmethylation-specific primer pairs useful for amplification of a methylated or an unmethylated SOCS-1 gene sequence (see SEQ ID NO:1; see, also, GenBank Acc. No. U15422), as well as for other SOCS/CIS gene sequences, which are well known in the art, can be readily made.

Accordingly, in one aspect, MSP is used for detecting the amount or distribution of uracil residues in a bisulfite ion treated SOCS/CIS gene following alkaline treatment. Such a method can be performed by contacting the SOCS/CIS gene sequence with a first amplification primer pair and a second amplification primer pair under conditions suitable for amplification, wherein the first amplification primer pair comprises a forward primer and a reverse primer, and at least one primer of the first primer pair comprises an oligonucleotide that selectively hybridizes to a SOCS/CIS gene sequence containing uracil residues, and wherein the second amplification primer pair comprises a forward primer and a reverse primer, and both primers of the second primer pair selectively hybridize to a SOCS/CIS gene sequence containing cytosine residues, but not to a SOCS/CIS gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the SOCS/CIS gene of the test cell.

The methods of the invention are exemplified herein with respect to identifying a neoplastic cell, which exhibits unregulated growth, wherein the method comprises detecting methylation of a cytosine residue of a CpG dinucleotide in a CpG island of a suppressor of cytokine signaling-1 (SOCS-1) gene in a sample comprising a test cell, or an extract thereof, whereby methylation of the SOCS-1 gene results in a reduced level of transcription and, therefore, expression of the SOCS-1 gene product in the test cell as compared to a corresponding normal cell. The neoplastic cell can be a premalignant cell or a cancer cell, for example, a hepatocellular carcinoma cell, a multiple myeloma cell, or an acute leukemia cell. The sample to be examined can be obtained from a subject such as a human subject, a domesticated animal, a farm animal, or the like, and can contain a cell suspected of being a neoplastic cell, or can contain nucleic acid molecules including a SOCS-1 gene sequence or a portion thereof comprising a CpG island. As such, the sample can be an organ sample, a tissue sample, or a cell sample, for example, a liver sample, a skin sample, a lymph node sample, a kidney sample, a lung sample, a muscle sample, a bone sample, or a brain sample; or can be a sample of a biological fluid, for example, bone marrow, blood, serum, lymph, cerebrospinal fluid, saliva, sputum, stool, urine, or ejaculate.

Methylation of a CpG dinucleotide in a SOCS-1 gene can be detected by contacting a nucleic acid molecule comprising the SOCS-1 gene of the test cell with a methylation sensitive restriction endonuclease that specifically binds a recognition site containing a CpG dinucleotide, and that either cleaves or does not cleave the recognition site depending on the methylation status of the cytosine residue of CpG dinucleotide. Methylation of a CpG dinucleotide in a SOCS-1 gene also can be detected by contacting a nucleic acid molecule comprising the SOCS-1 gene of the test cell with a chemical reagent such as hydrazine or sodium bisulfite and detecting the reaction products as discussed above.

Where the SOCS-1 gene sequence is treated using the bisulfite method, the amount or distribution of uracil residues then can be detected, for example, by determining the nucleotide sequence of the bisulfite ion treated SOCS-1 gene sequence following exposure to alkaline conditions. The bisulfite ion treated SOCS-1 gene sequence can be determined directly, or can be amplified using an amplification primer pair, for example, an amplification primer pair selected from SEQ ID NO:6 and SEQ ID NO:7; SEQ ID NO:12 and SEQ ID NO:13; SEQ ID NO:14 and SEQ ID NO:15; and SEQ ID NO:16 and SEQ ID NO:17, and the nucleotide sequence of the amplification product can be determined.

The amount or distribution of uracil residues also can be detected by contacting the sodium bisulfite treated SOCS-1 gene sequence, following exposure to alkaline conditions, with an oligonucleotide that selectively hybridizes to a SOCS-1 gene sequence containing uracil residues, for example, an oligonucleotide as set forth in SEQ ID NO:2, and detecting selective hybridization of the oligonucleotide; or by contacting the SOCS-1 gene sequence with an amplification primer pair including a methylation specific primer pair such as the primer pair set forth as SEQ ID NO:2 and SEQ ID NO:3, whereby generation of an amplification product is indicative of methylation of cytosine residues in CpG dinucleotides in the SOCS-1 gene of the test cell, or with an unmethylation specific amplification primer pair such as the primer pair set forth as SEQ ID NO:4 and SEQ ID NO:5, whereby generation of an amplification product is indicative of a lack of methylation of cytosine residues in CpG dinucleotides in the SOCS-1 gene of the test cell, thereby identifying the test cell as a neoplastic cell.

In one embodiment, the amplification reaction comprises a multiplex analysis, which can be performed, for example, by contacting the SOCS-1 gene sequence with at least two amplification primer pairs, including a methylation-specific amplification primer pair such as the primer pair set forth as SEQ ID NO:2 and SEQ ID NO:3, and an unmethylation-specific amplification primer pair such as the primer pair set forth as SEQ ID NO:4 and SEQ ID NO:5, under conditions suitable for amplification. The methylation-specific and unmethylation-specific primer pairs are selected such that an amplification product, if any, generated by the methylation-specific amplification primer pair has a first length, and an amplification product, if any, generated by the unmethylation-specific amplification primer pair has a second length, which is different from the first length. As such, generation of an amplification product having the first length is indicative of methylation of cytosine residues in CpG dinucleotides in the SOCS-1 gene of the test cell, thereby identifying the test cell as a neoplastic cell, whereas generation of an amplification product having the second length is indicative of a lack of methylation of cytosine residues in CpG dinucleotides in the SOCS-1 gene of the test cell, thereby identifying that the test cell is not a neoplastic cell.

The diagnostic methods of the invention are particularly adaptable to being performed in a high throughput format, wherein a plurality of test cells, or extracts of the test cells, or test cells and extracts thereof can be examined in parallel, preferably under automated or semi-automated conditions. Generally, the reactions in a high throughput assay are performed on a solid support such as microchip, a glass slide, a bead, or the like, wherein the individual samples are substantially isolated from each other. In addition, the samples generally are arranged in an array or other reproducible pattern, such that each sample can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

The present invention also provides reagents useful for practicing the diagnostic methods of the invention, including, for example, an isolated oligonucleotide, which is useful as a probe or a primer for detecting methylation (or the absence thereof) of a SOCS/CIS gene sequence, or in combination as amplification primer pairs for amplifying all or a portion of a SOCS/CIS gene sequence, particularly all or a portion of a CpG island of the gene, including a methylated SOCS-1 gene sequence or an unmethylated SOCS-1 gene sequence. Oligonucleotides useful for detecting SOCS-1 gene methylation are designed to be of sufficient length and having an appropriate sequence such that they can selectively hybridize to a target nucleic acid sequence, particularly a nucleotide sequence of a SOCS/CIS gene that comprises, or is upstream or downstream of a CpG island of the SOCS/CIS gene. Where the oligonucleotide is to be used as a substrate for a primer extension reaction, including an amplification reaction, the oligonucleotide is designed to allow specific initiation and extension by a polymerase.

As used herein, the term "oligonucleotide" or "polynucleotide" is used broadly to mean a sequence of two or more deoxyribonucleotides or ribonucleotides that are linked together by a phosphodiester bond. For convenience of discussion, the term "oligonucleotide" is used herein to refer to a polynucleotide that is used as a probe or primer, whereas the term "polynucleotide" is used more broadly to encompass any sequence of two or more nucleotides, including an oligonucleotide. As such, the terms include RNA and DNA, which can be a gene or a portion thereof, a cDNA, a synthetic polydeoxyribonucleic acid sequence, or the like. Generally, an oligonucleotide or polynucleotide can be single stranded or double stranded, as well as a DNA/RNA hybrid, although it will be recognized that the strands of a double stranded oligonucleotide that is to be used as a probe or primer will be separated, for example, by heating a solution containing the oligonucleotide above the melting temperature of the particular oligonucleotide.

The terms "oligonucleotide" and "polynucleotide" as used herein include naturally occurring nucleic acid molecules, which can be isolated from a cell, as well as fragments thereof as produced, for example, by a restriction endonuclease digestion, and synthetic molecules, which can be prepared, for example, by methods of chemical synthesis or by enzymatic methods such as by PCR. In various embodiments, an oligonucleotide or polynucleotide of the invention can contain nucleoside or nucleotide analogs, or a backbone bond other than a phosphodiester bond, for example, a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994); Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium, a cell or in a living subject, since the modified polynucleotides can be designed to be less (or, if desired, more) susceptible to degradation.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide (or oligonucleotide) also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). As such, the polynucleotide can be prepared using a method such as conventional phosphotriester and phosphodiester methods, including, for example, an automated method such as that using diethylphosphoramidites (see Beaucage et al., *Tetrahedron Lett.*, 22:1859-1862, 1981), or a method whereby the oligonucleotides are synthesized on a modified solid support (see U.S. Pat. No. 4,458,066).

An oligonucleotide of the invention, which can selectively hybridize to a target nucleic acid molecule and can be used as a reagent for detecting methylation of a SOCS/CIS gene such as SOCS-1, is designed to selectively hybridize to a nucleotide sequence within about 2000 nucleotides upstream (5') or downstream (3') of the target SOCS/CIS gene, and generally within about 1000 nucleotides of the region comprising the CpG island that is to be examined for cytosine methylation, usually within about 500 nucleotides of the site to be examined. In addition, an oligonucleotide of the invention, or useful in a method of the invention, is at least about 12 nucleotides in length, generally at least about 14 or 15 nucleotides in length, and usually at least about 18 to 20 nucleotides, such that it can selectively hybridize to the target nucleic acid molecule. It will be recognized that the length of the oligonucleotide will depend, in part, on the target SOCS/CIS gene. For example, when the target SOCS/CIS gene is one of a family of closely related genes having regions of substantial sequence similarity, a longer oligonucleotide can be used to assure selective hybridization to the target oligonucleotide and minimal, if any, cross-hybridization to the related gene sequence(s).

Oligonucleotides of the invention are designed to be substantially complementary to each strand of the genomic locus to be amplified and, where they are to be used for differentiating methylated from unmethylated cytosine residues, will include the appropriate guanine or cytosine residues, as discussed above. Oligonucleotides of the invention are exemplified herein by those having nucleotide sequences as set forth in SEQ ID NOS:6, 7, and 12 to 17, as well as those set forth in SEQ ID NOS:2 to 5, which can be used to differentiate a target sequence containing methylated cytosine residues of a CpG dinucleotide from one containing unmethylated cytosine residues.

Accordingly, the present invention provides an oligonucleotide selected from any one of SEQ ID NOS:2 to 6 and 12 to 17, and further provides a plurality of such oligonucleotides, which includes at least two (e.g., 2, 3, 4, 5, or more) of the oligonucleotides set forth as SEQ ID NOS:2 to 6 and 12 to 17. The present invention also provides an amplification primer pair, which comprises a forward primer and a reverse primer, particularly a primer pair that includes one of SEQ ID NOS:2 to 6 and 12 to 17, which can be a forward primer or a reverse primer of the primer pair. Amplification primer pairs of the invention are exemplified herein by those set forth as SEQ ID NOS:2 and 3; SEQ ID NOS: 4 and 5; SEQ ID NOS:6 and 7; SEQ ID NOS:12 and 13; SEQ ID NOS:14 and 15; and SEQ ID NOS:16 and 17. Furthermore, the present invention provides a plurality of amplification primer pairs, which includes at least one of the primer pairs set forth as SEQ ID NO:2 and SEQ ID NO:3; SEQ ID NO: 4 and SEQ ID NO:5; SEQ ID NO:6 and SEQ ID NO:7; SEQ ID NO:12 and SEQ ID NO:13; SEQ ID NO:14 and SEQ ID NO:15; or SEQ ID NO:16 and SEQ ID NO:17, and a second primer pair, which can, but need not, be one of the above listed primer pairs.

Primer pairs of the invention further include methylation-specific primer pairs, which only amplify a region of a CpG island of SOCS/CIS gene containing methylated cytosine residues in CpG dinucleotides in the CpG island; and unmethylation-specific primer pairs, which amplify a region of a CpG island of SOCS/CIS gene containing unmethylated cytosine residues in CpG dinucleotide in the CpG island. A methylation-specific primer pair of the invention is exemplified herein by the primer pair set forth in SEQ ID NOS:2 and 3, which can be used to specifically amplify a methylated SOCS-1 gene sequence. An unmethylation-specific primer pair of the invention is exemplified herein by the primer pair set forth as SEQ ID NOS:4 and 5, which can be used to specifically amplify an unmethylated SOCS-1 gene sequence. As such, it will be recognized that a plurality of primer pairs of the invention can include at least a first primer pair that is a methylation-specific primer pair such as the primer pair set forth as SEQ ID NOS:2 and 3, and a second primer pair that is an umethylation-specific primer pair such as the primer pair set forth as SEQ ID NOS:4 and 5. In one embodiment, such a plurality of primer pairs includes the primer pairs set forth as SEQ ID NOS:2 and 3, and SEQ ID NOS:4 and 5. It should further be recognized that a plurality of primer pairs can include at least a first primer pair such as one of the primer pairs exemplified by SEQ ID NO:2 and SEQ ID NO:3; SEQ ID NO:4 and SEQ ID NO:5; SEQ ID NO:6 and SEQ ID NO:7; SEQ ID NO:12 and SEQ ID NO:13; SEQ ID NO:14 and SEQ ID NO:15; or SEQ ID NO:16 and SEQ ID NO:17; and a second primer pair that includes oligonucleotides that selectively hybridize to an amplification product generated using the first amplification primer pair, thus providing reagents useful for performing a nested amplification procedure.

The present invention also provides kits that contain one or more reagents useful for practicing a method of the invention. As such, a kit of the invention can contain, for example, one or more oligonucleotides that selectively hybridize to or near a CpG island of a SOCS/CIS gene, e.g., one or more of SEQ ID NOS:2 to 6 and 12 to 17. Such a kit can be useful for preparing a probe that selectively hybridizes to the particular SOCS/CIS gene sequence, in which case the kit can further contain, for example, a detectable label that can be linked to or incorporated into the probe, or a plurality of different detectable labels such that, depending the needs of the user, can be selected for a particular use, and, if desired, reagents for linking or incorporating the detectable label into the oligonucleotide. Alternatively, or in addition, the kit can contain one or more reagents useful for performing a hybridization reaction such that selective hybridization conditions readily are attained; and/or can contain one or more standard nucleic acid molecules, for example, a standard target SOCS-1 nucleotide sequence that contains methylated cytosine residues corresponding the region to which the oligonucleotide is designed to selectively hybridize, or a standard target SOCS-1 nucleotide sequence that contains unmethylated cytosine residues corresponding to the target sequence, or a combination thereof. Such standards provide several advantages, including, for example, allowing a confirmation that a reaction using a test cell, or extract thereof, functioned properly, or allowing for comparisons among samples examined at different times or collected from different sources.

A kit containing one or more oligonucleotides of the invention such as one or more of SEQ ID NOS:2 to 6 and 12 to 17 also can be useful for performing a primer extension reaction. As such, the kit can further include reagents for performing the selective hybridization reaction such that the oligonucleotide provides a substrate for the extension reaction; and/or one or more reagents for performing the primer extension reaction, for example, dNTPs, one or more of which can be detectably labeled or otherwise modified for conveniently linking a detectable label; and/or one or more standard target nucleic acid molecules, as discussed above. Where a kit of the invention contains two or more oligonucleotides (or primer pairs) such as those exemplified herein or otherwise useful for practicing the methods of the invention, the kit provides a convenient source of reagents from which the skilled artisan can select one or more oligonucleotides (or primer pairs), as desired.

As such, a kit of the invention also can at least one amplification primer pair useful for detecting the presence or absence of methylated cytosine residues in a CpG dinucleotide of a CpG island of a SOCS/CIS gene. Amplification primer pairs that can be included in a kit of the invention are exemplified by those set forth in SEQ ID NO:2 and SEQ ID NO:3; SEQ ID NO: 4 and SEQ ID NO:5; SEQ ID NO:6 and SEQ ID NO:7; SEQ ID NO:12 and SEQ ID NO:13; SEQ ID NO:14 and SEQ ID NO:15; and SEQ ID NO:16 and SEQ ID NO:17. Such kits of the invention are further exemplified by a kit containing a plurality of primer pairs, including a methylation-specific primer pair and an unmethylation-specific primer pair, for example, a kit containing the primer pairs set forth as SEQ ID NOS:2 and 3, and SEQ ID NOS:4 and 5. Such a kit also can contain reagents for providing conditions suitable for performing an amplification reaction, including, for example, dNTPs, one or a selection of polymerases, buffers, detectable labels, one or more standard target nucleic acid molecules, a chemical reagent that differentially modifies methylated as compared to unmethylated cytosine residues, a methylation sensitive restriction endonuclease. and the like.

As disclosed herein, methylation of CpG dinucleotides in a CpG island of a SOCS/CIS gene such as SOCS-1 is associated with loss of regulation of cell growth, including cancer. Accordingly, the invention provides methods for selecting a therapeutic strategy for treating a cancer patient by detecting methylation-silenced transcription of a SOCS/CIS gene in cancer cells of the patient. Such a method can be performed by examining a sample suspected of containing cancer cells from the patient for decreased expression of a SOCS/CIS gene product due to methylation-silenced transcription, whereby the detection of decreased expression of a SOCS/CIS gene product indicates selecting an agent that restores the SOCS/CIS gene product to the cancer cells as a component of the therapeutic strategy.

Upon determining that a cancer is associated with methylation-silenced transcription of a SOCS/CIS gene, the agent selected for restoring SOCS/CIS gene product to the cell can be an agent that acts generally, for example, a demethylating agent, which restores transcriptional activity of the silenced SOCS/CIS gene, or an agent that modulates the activity of an effector molecule downstream of the SOCS/CIS gene in a signal transduction pathway, for example, an agent such as AG490, which inhibits JAK kinase activity. The agent to be selected also can be a more specific agent that is selected based on the particular SOCS/CIS gene that is methylation-silenced. For example, where the cancer is associated with methylation-silenced SOCS-1 gene expression, the agent can be the SOCS-1 protein, or a polynucleotide encoding SOCS-1, such as the polynucleotide set forth in SEQ ID NO:1, or a substantially similar polynucleotide that has silent nucleotide changes that change a codon to a degenerate codon encoding the same amino acid.

Accordingly, the present invention also provides methods for reducing or inhibiting unregulated growth of a cell exhibiting methylation silenced transcription of a SOCS/CIS gene, including methods that can be performed in vitro or in vivo, and can be used for treating an individual suffering from a disorder associated with such unregulated growth, for example, a cancer patient, thereby providing a means to ameliorate the severity of the disorder. The present invention also provides compositions useful for practicing such methods and, therefore, further provides medicaments, which are useful for restoring methylation-silenced transcription of a SOCS/CIS gene.

As a result of methylation-silenced transcription of a SOCS/CIS gene in a cell, the SOCS/CIS gene product is not present in the cell and, therefore, signal transduction pathways that include the SOCS/CIS gene product can exhibit aberrant regulation. For example, methylation-silenced transcription of the SOCS-1 gene results in constitutively activated JAK2 kinase due to absence of the SOCS-1 protein, which down-regulates JAK2 activity, and unregulated growth of the cell, which can be due, at least in part, to a decreased level of apoptosis. Accordingly, the methods of the invention are based on providing a cell that exhibits unregulated growth due to methylation-silenced transcription of a SOCS/CIS gene with the polypeptide encoded by the methylation-silenced SOCS/CIS gene, thereby restoring regulated growth to the cell. As disclosed herein, the polypeptide can be provided to the cell directly, can be expressed from an exogenous polynucleotide that is introduced into the cell and encodes the polypeptide, or by restoring expression of the endogenous methylation-silenced SOCS/CIS gene in the cell. By restoring the SOCS/CIS polypeptide to a cell exhibiting unregulated growth, or characteristics generally associated with unregulated growth, including, for example, the ability to grow in soft agar, a lack of contact inhibited growth, or refractoriness to programmed cell death, are alleviated.

A method of the invention can be practiced by restoring expression of the methylation-silenced SOCS/CIS gene in the cell. Such a method can be practiced, for example, by contacting the cells with a demethylating agent such as 5-azacytidine, which, when incorporated into the SOCS/CIS gene during replication of a cell containing a methylation-silenced SOCS/CIS gene, results in progeny cells containing an unmethylated SOCS/CIS gene. The cells contacted with the demethylating agent can be cells in culture, wherein the demethylating agent is added to the cell culture medium in an amount sufficient to result in demethylation of the SOCS/CIS gene, without being toxic to the cells. The cells in culture can be cells of an established cell line, or can be cells, which can be a mixed population of cells, that have been removed from a subject and are being contacted ex vivo, for example, to determine whether contact with the particular demethylating agent can restore the SOCS/CIS gene expression, and therefore, can be useful when administered to the subject. Such ex vivo treatment of the cells also can be useful for restoring SOCS/CIS gene expression, after which the cells, which optionally can be expanded in culture, can be administered back to the subject. For example, bone marrow cells can be obtained by an aspiration or other method from an individual suffering from multiple myeloma or an acute leukemia, treated ex vivo with the demethylating agent, then administered back into the subject. Such a method, as well as any of the methods of treatment as disclosed herein, can further include treatments otherwise known in the art as useful for treating a subject having the particular cancer, or that can be newly useful when used in combination with the present methods. For example, a patient with an acute leukemia can be treated with a chemotherapeutic agent or with whole body radiotherapy to destroy leukemia cells in the body, then the ex vivo treated bone marrow cells, which comprises cells having restored SOCS/CIS gene expression, can be administered back into the patient.

Cells exhibiting methylation-silenced SOCS/CIS gene expression also can be contacted with the demethylating agent in vivo by administering the agent to a subject. Where convenient, the demethylating agent can be administered using, for example, a catheterization procedure, at or near the site of the cells exhibiting unregulated growth in the subject, or into a blood vessel in which the blood is flowing to the site of the cells. Similarly, where an organ to be treated can be isolated by a shunt procedure, the agent can be administered via the shunt, thus substantially providing the agent to the site containing the cells. The agent also can be administered systemically or via other routes as disclosed herein or otherwise known in the art.

A method of providing a SOCS/CIS polypeptide to a cell also can be performed by introducing a polynucleotide encoding the SOCS/CIS polypeptide into the cell, whereby the SOCS/CIS polypeptide is expressed from the polynucleotide. As such, the present invention provides methods of gene therapy, which can be practiced in vivo or ex vivo. For example, where the cell is characterized by methylation-silenced transcription of the SOCS-1 gene, a polynucleotide comprising SEQ ID NO:1 can be contacted with the target cell.

The polynucleotide encoding the SOCS/CIS polypeptide can include, in addition to SOCS/CIS polypeptide coding sequence, operatively linked transcriptional regulatory elements, translational regulatory elements, and the like, and can be in the form of a naked DNA molecule, or can be formulated in a matrix that facilitates entry of the polynucleotide into the particular cell, for example, a liposome, in which case the polynucleotide contains the required operatively linked regulatory elements. As used herein, the term "operatively linked" refers to two or more molecules are positioned with respect to each other such that they act as a single unit and effect a function attributable to one or both molecules or a combination thereof. For example, a polynucleotide encoding a SOCS-1 polypeptide can be operatively linked to a second (or more) coding sequence, such that a chimeric polypeptide can be expressed from the operatively linked coding sequences. The chimeric polypeptide can be a fusion protein, in which the two (or more) encoded polypeptides are translated into a single polypeptide, i.e., are covalently bound through a peptide bond; or can be translated as two discrete peptides that, upon translation, can operatively associate with each other to form a stable complex. Similarly, a polynucleotide sequence encoding a SOCS/CIS polypeptide can be operatively linked to a regulatory element, in which case the regulatory element confers its regulatory effect on the polynucleotide similarly to the way in which the regulatory element would effect a polynucleotide sequence with which it normally is associated with in a cell.

A fusion protein generally demonstrates some or all of the characteristics of each of its polypeptide components, and, therefore, can be useful for restoring SOSC/CIS gene expression in the cell and can further provide additional advantages. For example, the fusion protein can include a SOCS-1 polypeptide operatively linked to a cell compartment localization domain such that expression of the fusion protein in a cell or loading of the cell with fusion protein allows translocation of the SOCS-1 polypeptide (or other SOCS/CIS polypeptide) to the intracellular compartment such as the nucleus, in which it effects its activity. Cell compartmentalization domains, for example, are well known and include a plasma membrane localization domain, a nuclear localization signal, a mitochondrial membrane localization signal, an endoplasmic reticulum localization signal, and the like, as well as signal peptides, which can direct secretion of a polypeptide from a cell (see, for example, Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). The fusion protein also can comprise a SOCS/CIS polypeptide operatively linked to a peptide that acts as a ligand for a receptor, a peptide useful as a tag for identifying a cell containing the SOCS/CIS polypeptide, or for isolating the fusion protein, or any other peptide or polypeptide of interest, providing the fusion protein has the SOCS/CIS protein activity for which it is being expressed, e.g., to reduce or inhibit constitutive JAK activity. Peptide tags such as a polyhistidine tag peptide, e.g., His-6, which can be detected using a divalent cation such as nickel ion, cobalt ion, or the like; a FLAG epitope, which can be detected using an anti-FLAG antibody (see, for example, Hopp et al., *Bio-Technology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione, are well known in the art, and provide a means of detecting the presence of a SOCS/CIS polypeptide operatively linked thereto. Such tags provide the additional advantage that they can facilitate isolation of the operatively linked SOCS/CIS polypeptide, for example, where it is desired to obtain the SOCS/CIS polypeptide in a substantially purified form, such a polypeptide also being useful for practicing methods of the invention.

A polynucleotide encoding a SOCS/CIS gene product can be used alone, or can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and encoded SOCS/CIS polypeptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide encoding the SOCS/CIS polypeptide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A tetracycline (tet) inducible promoter can be particularly useful for driving expression of a polynucleotide encoding a SOCS/CIS polypeptide. Upon administration of tetracycline, or a tetracycline analog, to a subject containing a polynucleotide operatively linked to a tet inducible promoter, expression of the encoded SOCS/CIS polypeptide is induced. The polynucleotide also can be operatively linked to tissue specific regulatory element, for example, a liver cell specific regulatory element such as an I-fetoprotein promoter (Kanai et al., *Cancer Res.* 57:461-465, 1997; He et al., *J. Exp. Clin. Cancer Res.* 19:183-187, 2000) or an albumin promoter (Power et al., *Biochem. Biophys. Res. Comm.* 203:1447-1456, 1994; Kuriyama et al., *Int. J. Cancer* 71:470-475, 1997); a muscle cell specific regulatory element such as a myoglobin promoter (Devlin et al., *J. Biol. Chem.* 264:13896-13901, 1989; Yan et al., *J. Biol. Chem.* 276:17361-17366, 2001); a prostate cell specific regulatory element such as the PSA promoter (Schuur et al., *J. Biol. Chem.* 271:7043-7051, 1996; Latham et al., *Cancer Res.* 60:334-341, 2000); a pancreatic cell specific regulatory element such as the elastase promoter (Ornitz et al., *Nature* 313:600-602, 1985; Swift et al., *Genes Devel.* 3:687-696, 1989); a leukocyte specific regulatory element such as the leukosialin (CD43) promoter (Shelley et al., *Biochem. J.* 270:569-576, 1990; Kudo and Fukuda, *J. Biol. Chem.* 270:13298-13302, 1995); or the like, such that expression of the polypeptide is restricted to particular cell in an individual, or to particular cells in a mixed population of cells in culture, for example, an organ culture. Regulatory elements, including tissue specific regulatory elements, many of which are commercially available, are well known in the art (see, for example, InvivoGen; San Diego Calif.).

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a SOCS/CIS polypeptide can be cloned into a baculovirus vector, which then can be used to infect an insect host cell, thereby providing a means to produce large amounts of the encoded polypeptide. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, hepatitis virus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

A polynucleotide, which can be contained in a vector, can be introduced into a cell by any of a variety of methods known in the art (Sambrook et al., supra, 1989; Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. A polynucleotide of the invention, or a vector containing the polynucleotide can be contained in a cell, for example, a host cell, which allows propagation of a vector containing the polynucleotide, or a helper cell, which allows packaging of a viral vector containing the polynucleotide. The polynucleotide can be transiently contained in the cell, or can be stably maintained due, for example, to integration into the cell genome.

A method of the invention also can be practiced by directly providing SOCS/CIS polypeptide to a cell exhibiting unregulated growth. The SOCS/CIS polypeptide can be produced and isolated, and formulated as desired, using methods as disclosed herein. The polypeptide can be contacted with the cell in vitro under conditions that result in sufficient permeability of the cell such that the polypeptide can cross the cell membrane, or can be microinjected into the cells. Where the SOCS/CIS polypeptide is contacted with a cell in situ in an organism, it can comprise a fusion protein, which includes a peptide or polypeptide component that facilitates transport across the cell membrane, for example, a human immunodeficiency virus (HIV) TAT protein transduction domain, and can further comprise a nuclear localization domain operatively linked thereto. Alternatively, or in addition, the polypeptide can be formulated in a matrix that facilitates entry of the polypeptide into a cell.

In one embodiment, the invention provides a method of treating a subject suffering from hepatocellular carcinoma (HCC) or multiple myeloma (MM), wherein cells associated with the HCC or MM exhibit methylation silenced SOCS-1 gene expression, the method comprising administering an amount of AG490 to the subject sufficient to induce apoptosis of the cells associated with the cancer. In another embodiment, the invention provides a method for treating a cancer patient, wherein cancer cells in the patient exhibit methylation silenced SOCS-1 gene expression, by providing SOCS-1 polypeptide (SEQ ID NO:20) to the cancer cells, thereby inducing apoptosis of the cells. SOCS-1 polypeptide can be provided to the cancer cells by contacting the cells with a demethylating agent, for example, by administering the demethylating agent to the subject in an amount sufficient to restore SOCS-1 gene expression in the cancer cells, or by introducing a polynucleotide encoding SOCS-1, for example, the polynucleotide set forth as SEQ ID NO:1 or a polynucleotide encoding SEQ ID NO:20, into the cancer cells under conditions sufficient for expression of the encoded SOCS-1 polypeptide in the cancer cells. Where the polynucleotide is administered to a subject, the polynucleotide can be contained in a vector, particularly a vector derived from a virus that preferentially infects the cells from the cancer cells arose, for example, a vector derived from or containing components of a hepatitis virus where the cancer cells are hepatocellular carcinoma cells, or a vector derived from or containing components of HIV where the cancer cells are T cell leukemia cells. The polynucleotide, which can be contained in a vector, also can be formulated with a matrix such as a liposome, which can be further modified to contain a receptor (or ligand) on its surface, wherein the receptor (or ligand) can specifically bind a cognate ligand (or receptor) expressed by the cancer cells, for example, the liposome can contain on its surface antibodies such as anti-idiotype antibodies that specifically binds with antibodies expressed by plasma cells associated with a multiple myeloma, or can contain a ligand that specifically with an apolipoprotein expressed by hepatocytes.

For administration to a living subject, an agent such as a demethylating agent, AG490, a polynucleotide encoding a SOCS/CIS gene, or a SOCS/CIS polypeptide useful for practicing a therapeutic method of the invention generally is formulated in a composition suitable for administration to the subject. Thus, the invention provides compositions containing an agent that is useful for restoring regulated growth to a cell exhibiting unregulated growth due to methylation-silenced transcription of a SOCS/CIS gene. As such, the agents are useful as medicaments for treating a subject suffering from a pathological condition associated with such unregulated growth.

Such compositions generally include a carrier that can is acceptable for formulating and administering the agent to a subject. Such acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of an acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of the composition containing the therapeutic agent will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are disclosed herein or otherwise known in the art (see, for example, Blondelle et al., supra, 1995; Ecker and Crook, supra, 1995). In addition, a polypeptide agent can be prepared using D-amino acids, or can contain one or more domains based on peptidomimetics, which are organic molecules that mimic the structure of a domain; or based on a peptoid such as a vinylogous peptoid.

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The following examples are intended to illustrate, but not limit, the invention.

EXAMPLE 1

Methylation of SOCS-1 is Associated with Hepatocellular Carcinoma

This example demonstrates that hypermethylation of the SOCS-1 gene and consequent decreased expression of SOCS-1 correlate with unregulated growth of hepatocellular carcinoma (HCC) cells, and that agents that circumvent the decreased SOCS-1 expression induce apoptosis of the HCC cells.

Methods

Cell Lines and Tissue Samples

Human hepatocellular carcinoma cell (HCC) lines SNU-182, SNU-423, SNU-387, SNU-398, SNU-449, SNU-475, and PLC/PRF/5 were obtained from American Type Culture Collection. GM06061C was obtained from NIGMS repository. HuH-1, HuH-4, HuH-7 and Hep3B were obtained from Japanese Culture Collection. The cells were grown in DMEM or RPMI 1640 supplemented with 10% fetal bovine serum (FBS) for isolation of DNA and RNA. Primary hepatocarcinoma samples and adjacent normal liver tissue are described by Rashid et al. (*Brit. J. Cancer* 80:59-66, 1999).

Northern Blot Analysis

Poly(A) RNA of HCC cell lines was prepared using the QuickPrep MICRO mRNA Purification Kit (Amersham Pharmacia Biotech). Normal liver poly(A) RNA was purchased from Clontech (Palo Alto Calif.). The 3' sequence of SOCS-1 (nucleotides 679 to 1031 of GenBank Acc. No. U88326; SEQ ID NO:1; see, also, Starr et al., supra, 1997) was used as a probe. Northern blot analysis was performed as described by Yoshikawa et al. (*Genomics* 49:237-246, 1998); full length SOCS-1 mRNA migrates with a size of about 1.3 kb. As a control, the same membrane was re-probed with a GAPD (G3PDH) probe (Clontech).

Methylation Specific PCR

Genomic DNA was extracted using a standard method, and bisulfite modification of genomic DNA was performed as by Herman et al. (*Proc. Natl. Acad. Sci. USA* 93:9821-9826, 1996). Methylation status of SOCS-1 was analyzed by methylation-specific PCR (MSP), which distinguishes unmethylated alleles from methylated alleles in a gene on the basis of sequence changes induced by sodium bisulfite treatment of DNA; bisulfite treatment converts all unmethylated, but not methylated, cytosine residues to uracil. The DNA region of interest then was amplified with primer pairs specific for methylated versus unmethylated DNA.

The bisulfite treated DNA was amplified either with a methylation-specific primer set or a unmethylation-specific primer set at 35 cycles for 95° C., 30 sec; 60° C., 30 sec; and 72° C., 30 sec.

The methylation specific primer sequences were as follows: forward primer-5'-TTCGCGTGTATTTTTAGGTCG-GTC-3' (SEQ ID NO:2), and reverse primer-5'-CGACA-CAACTCCTACAACGACCG-3' (SEQ ID NO:3). These primers were designed from nucleotides 400 to 423 (forward primer) and nucleotides 537 to 559 (reverse primer) of the SOCS-1 sequence (SEQ ID NO:1).

The unmethylation specific primer sequences were as follows:

```
                                         (SEQ ID NO: 4)
forward  5'-TTATGAGTATTTGTGTGTATTTTTAGGTTGGTT-3',
primer
and (SEQ ID NO: 5)
reverse  5'-CACTAACAACACAACTCCTACAACAACCA-3'.
primer
```

These primers were designed from nucleotides 391 to 423 (forward primer) and nucleotides 537 to 565 (reverse primer) of SEQ ID NO:1.

Amplification of methylated SOCS-1 using SEQ ID NOS:2 and 3 generates a 160 bp DNA product, whereas amplification of unmethylated SOCS-1 using SEQ ID NOS:4 and 5 generates a 175 bp product.

Sequencing Analysis

Bisulfite sequencing analysis was performed for 5 HCC cell lines and 2 non-tumor liver samples. Bisulfite treated DNA was amplified using the primer set: 5'-TGTAGGATG-GTAGTATATAATTAGGTGGT-3' (SEQ ID NO:6), and 5'-TAATACTCCAACAACTCTAAAAAACAATC-3' (SEQ ID NO:7), which was designed to amplify nucleotides 18 to 484 in SEQ ID NO:1. The PCR product was cloned into the pCR2.1-TOPO vector (Invitrogen Corp.; Carlsbad Calif.), and 4 to 8 randomly picked clones were sequenced using ABI PRISM Big Dye Terminator Cycle sequencing kit (Applied Biosystems, Inc.; Foster City Calif.) according to the protocol supplied by the manufacturer.

Preparations of the Matrix and PCR Analysis of the Matrix Associated DNA

Matrix was isolated as described by Kramer et al. (supra, 1998). Briefly, 2×10$^6$ cells were washed with phosphate buffered saline (PBS). Nuclei were isolated by treatment with a buffer containing 10 mM Tris (pH 7.7), 100 mM NaCl, 0.3 M sucrose, 3 mM MgCl$_2$ and 0.5% TRITON-X100 detergent, and collected by centrifugation at 500×g for 5 min. The nuclei were treated with 2M NaCl, 10 mM Tris pH 7.7 and 10 mM EDTA, and placed on ice for 15 min.

The resulting halo structure was recovered by centrifugation, and washed 3 times with a low salt buffer containing 10 mM Tris (pH 7.5), 10 mM MgCl$_2$ and 1 mM DTT. The halo was resuspended with the low salt buffer, and digested with 300 units of Sac I for 4 hr at 37° C. Complete digestion was assessed using a plasmid DNA as an internal marker. Digestion was terminated by addition of 0.5 M EDTA to a final concentration of 25 mM, then NaCl was added to a final concentration of 2M, and the sample was incubated at 37° C. for 15 min. The pellet and supernatant were fractionated by centrifugation at 12,000×g for 10 min. After washing the pellet, the matrix-attached DNA and matrix unattached DNA were extracted by proteinase K treatment, followed by phenol/chloroform extraction from the pellet and supernatant fraction, respectively.

Using 50 ng of DNA, PCR was carried out with 30 cycles at 94° C., 40 sec; 60° C., 1 min; and 72° C., 40 sec. The primers used for this method were as follows:

5'-AACACCCCAGCCATGTACG-3' (SEQ ID NO:8), and
  5'-ATGTCACGCACGATTTCCC-3' (SEQ ID NO:9), for ACTB, 5'-CAGCCCAGAGGAGCCTAAAG-3' (SEQ ID NO:10), and 5'-TCCAGTTCAGGGTGCCATAC-3' (SEQ ID NO:11) for human protamine 1 (PRM1; amplifies nucleotides 9112 to 9304 of GenBank Acc. No. U15422); and 5'-TTCTCTCACCCCCTCACGC-3'(SEQ ID NO:12), and
  5'-GCTGGGCACTTGGTTACTGG-3' (SEQ ID NO:13) for SOCS-1 (amplifies nucleotides 38526 to 38834 of GenBank Acc. No. U15422, which is incorporated herein by reference; see, also, Nelson and Krawetz, *J. Biol. Chem.* 269:31067-31073, 1994; Kramer and Krawetz, *BioTechniques* 22:826-828, 1997, each of which is incorporated herein by reference).

Immunoprecipitation and Western Blot Analysis

Cells at approximately 70% confluence were harvested and lysed on ice in a buffer containing 20 mM Tris (pH 8.0), 1% NONIDET P-40 detergent, 0.1% SDS, 150 mM NaCl, 50 mM NaF, 1 mM Na$_3$VO$_4$, 10 µg/ml leupeptin, 10 µg/ml aprotinin, 1 µg/ml pepstatin, and 1 mM phenylmethylsulfonyl fluoride. Following incubation for 30 min on ice, the lysates were cleared of debris by centrifugation at 15,000×g for 30 min. Eight hundred µg of protein lysates were incubated with 5 µg anti-JAK2 antibody (Upstate Biotechnology; Waltham Mass.) for 1 hr on ice. Thirty µl protein A+G (Oncogene Research Products; Boston Mass.) was added to the lysates and incubated for 1 hr at 4° C. with rotation.

Immune complexes were recovered by centrifugation, washed 5 times with the lysis buffer, then boiled for 5 min in SDS-PAGE sample buffer. The samples were resolved by SDS-PAGE, and electroblotted onto a nitrocellulose membrane. The blot was blocked with 5% skim milk in PBS for 1 hr at room temperature (RT), then incubated with 1 µg/ml of anti-phosphotyrosine antibody (4G10; Upstate biotechnology) over night at 4° C.

After several washes, a 1:5000 dilution of anti-mouse horseradish peroxidase-conjugated secondary antibody (Amersham Pharmacia Biotech) was added and incubated for 1 hr at RT. After several washes, the immunoreactive bands were visualized by an enhanced chemiluminescence substrate (Amersham Pharmacia Biotech) and exposed to HYPER-FILM film (Amersham Pharmacia Biotech). The blot was stripped with a buffer composed of 62.5 mM Tris (pH 6.8), 2% SDS and 100 mM θ-mercaptoethanol at 50° C. for 30 min, washed, blocked with 5% milk in PBS, then re-probed with the anti-JAK2 antibody (Upstate Biotechnology).

To analyze inhibition of STAT3 by AG490, cells were treated with 25 µM AG490 for 3 hr or 24 hr. Eighty µg total protein samples from drug treated and untreated cells were separated by SDS-PAGE, and analyzed by western blot analysis. Anti-phospho-STAT3 antibody (New England Biolabs) was used to detect tyrosine phosphorylation of STAT3 according to the conditions recommended by the manufacturer. After removing the antibody, the blot was analyzed with anti-STAT3 antibody (Santa Cruz Biotechnology).

Construction of Human SOCS-1 Expression Vector

A full length SOCS-1 cDNA was isolated from human embryonic liver RNA (Clontech) by PCR using the following primer set:

5'-CCCCTTCTGTAGGATGGTAG-3' (SEQ ID NO:14), and
  5'-CATCCCAGTTAATGCTGCGT-3' (SEQ ID NO:15).
The PCR product was cloned into the pCR3.1 vector (Invitrogen). The full length SOCS-1 cDNA was excised from the recombinant vector with Eco RI, and ligated with Eco RI-digested pcDNA3.1/H is C vector (Invitrogen). A clone, pcDNA-SOCS-1, contained an in-frame ligation with the sense orientation and a correct sequence when compared to GenBank Acc. No. U88326 (SEQ ID NO:1).

Transfection Experiments and Colony Formation Assay with AG490

For colony formation in monolayer culture analysis, cells were plated at 30×10⁴ cells per well in 6 well plates, and transfected with 5 μg of either pcDNA3.1-SOCS-1 or the backbone pcDNA3.1 vector (control) using the LipofectAMINE PLUS transfection reagent (Invitrogen Corp.) according to the protocol provided by the manufacturer. The cells were stripped and plated on 100 mm tissue culture at 48 hours post-transfection. The cells were selected with G418 antibiotic at a concentration of 500 μg/ml, and the colonies were counted 4 weeks after transfection.

For colony formation in soft agar analysis, cells were transfected as above, and suspended in RPMI 1640 containing 0.35% agar, 10% fetal bovine serum and 500 μg/ml G418, and layered on RPMI 1640 containing 0.5% agar, 10% fetal bovine serum and 500 μg/ml G418 in 100 mm tissue culture dishes at 48 hours post-transfection. An additional 0.35% fresh agar culture medium with 500 μg/ml G418 was layered every 5 days. Colony formation was assessed at 4 weeks post-transfection.

For AG490 treatment, 1×10⁴ cells were plated in 100 mm tissue culture dishes, and grown in complete medium in the absence or presence of 5 μM AG490 for 3 weeks. In some experiments, cells were treated with 25 μM AG490 for 3 hr or 24 hr.

Immunofluorescence Analysis

Approximately 3000 cells were seeded in an eight well chamber slide, and transfected with 200 ng pcDNA3.1-SOCS-1 using the LipofectAMINE PLUS transfection reagent. At two days post-transfection, a TUNEL reaction was performed using the In situ Cell Death Detection Kit, Fluorescein kit (Roche Molecular Biochemicals) according to the protocol provided by the manufacturer. Subsequently, the cells were blocked for 1 hr with 3% BSA at RT, then incubated with a 1:200 dilution of anti-Xpress™ antibody (Invitrogen Corp.) for 1 hr at 37° C. After several washes, the cells were incubated with a 1:200 dilution of Texas red anti-mouse secondary antibody (Vector Laboratories; Burlingame Calif.). The cells were washed, and mounted in a medium (Vector Laboratories) containing 0.5 μg/ml DAPI, then viewed under a fluorescence microscopy at 60× magnification. Exogenously expressed SOCS-1 protein, fragmented DNA, and nuclei were identified under appropriate filters.

Results

Methylation in SOCS-1 CpG Island Correlates with Silencing of Gene Expression

Methylation of the SOCS-1 CpG island was analyzed in eleven different HCC cell lines. Methylation specific PCR (MSP) analysis revealed aberrant DNA methylation in 7 of the 11 HCC cell lines using a primer set that was designed in exon 1 and lies within the SOCS-1 CpG island. In contrast, one lymphoblast cell line and two non-tumor liver samples, including one from a cirrhotic liver and another from a patient with chronic hepatitis, did not show methylation in this region (see Yoshikawa et al., supra, 2001).

To examine DNA methylation patterns in the SOCS-1 CpG island in more detail, the HCC cell lines were examined using bisulfite sequencing. A total of 58 CpG sites in exon 1 were examined in the 467 base pair genomic sequence. HCC cell lines (Hep3B, PLC/PRF/5, and SNU-387), which were methylated when examined by MSP, also were densely methylated when examined by bisulfite sequencing. In addition, the HuH-1 cell line demonstrated a regional and clustering methylation; MSP did not detect methylation of this cell line because the CpG sites involved were not in the same region as that examined by MSP. In contrast, no significant methylation was detected in the two non-tumor liver samples or in the SNU-182 cells (see FIG. 1 in Yoshikawa et al., supra, 2001).

SOCS-1 expression in the HCC cell lines also was examined by northern blot analysis. Cell lines with fully unmethylated DNA (HuH-4, HuH-7 and SNU-182) and normal liver demonstrated substantial SOCS-1 expression. In contrast, the methylated cell lines, HuH-1, Hep3B, SNU-387, SNU-449, PLC/PRF/5 and SNU-398 (as detected by MSP or bisulfite sequencing) did not express SOCS-1. Interestingly, partially methylated cell lines (SNU-423 and SNU-475), in which half of the DNA was unmethylated, also expressed SOCS-1 (see Table 1). As a control, GAPD probing of the same filter demonstrated that the loading of the RNA was similar. These results indicate the expression status of SOCS-1 correlated with the methylation status of the SOCS-1 CpG island (Table 1); i.e., hypermethylation correlated with a lack of SOCS-1 gene expression.

TABLE 1

DNA methylation and RNA expression of SOCS-1

| Cell line | RNA expression | MSP ME | MSP UN | Bisulfite sequencing |
|---|---|---|---|---|
| HuH-1 | − | − | + | + |
| Hep3B | − | + | − | + |
| SNU-387 | − | + | − | + |
| SNU-449 | − | + | − | |
| PLC/PRF/5 | − | + | − | + |
| SNU-398 | − | + | − | |
| SNU-423 | + | + | + | |
| SNU-475 | + | + | + | |
| HuH-4 | + | − | + | |
| HuH-7 | + | − | + | |
| SNU-182 | + | − | + | − |
| normal | + | | | |

A '−' represents no expression and a '+' represents significant RNA expression in northern-blot analysis. 'ME' and 'UN' indicate results from MSP analysis for methylation and unmethylation reactions, respectively, with '−' indicating no product, whereas '+' indicates the presence of product. A '+' in bisulfite sequencing section represents methylation, and a '−' represents unmethylation.

Methylation Silencing is Associated with Alteration of the Matrix Association at the SOCS-1 CpG Island Specific regions of chromosomal DNA are believed to attach to the nuclear matrix, which is a fibrous protein network extending throughout the nuclear interior. A protamine gene cluster is located within 30 kb of the SOCS-1 gene. The matrix association at SOCS-1 and PRM1 are altered between sperm cells and somatic cells (Kramer et al., supra, 1998), suggesting that the matrix association of SOCS-1 is altered between the SOCS-1 methylated and unmethylated cells.

The matrix association at 3 loci in SOCS-1 methylated cells and SOCS-1 unmethylated cells was examined. The Actin B (ACTB) locus was used as a control for DNA attached to the nuclear matrix. To analyze the SOCS-1 and PRM1 loci, primers were designed to examine the 5' regions of these genes, where the functional matrix association was demonstrated (Kramer et al., supra, 1998). The two primer sets are separated by 38 kb. At the ACTB locus, a pellet fraction composed of matrix associated DNA showed equal intensity between the SOCS-1 methylated and unmethylated cells. At the PRM1 locus, an equal amount of matrix association also was observed in SOCS-1 methylated and unmethylated cells. At the SOCS-1 locus, in contrast, matrix associated DNA from the SOCS-1 unmethylated cells was greater than that from the SOCS-1 methylated cells (see FIG. 2 in Yoshikawa et al., supra, 2001). These results indicate that matrix association of the SOCS-1 gene was reduced in the SOCS-1 methylated cells.

Analysis of SOCS-1 CpG Island Methylation in Primary HCC Tissue Samples

Methylation of the SOCS-1 CpG island was examined in 26 surgically resected primary HCC samples. Of the 26 samples, five were paired (tumor/non-tumor); only tumor tissue was available for the remaining samples. None of the non-tumor liver samples showed methylation of SOCS-1, whereas methylation of SOCS-1 was detected in 4 of the 5 tumor samples from these paired samples. Methylation also was detected in 13 of the 21 samples for only tumor tissue was available (see FIG. 3 in Yoshikawa et al., supra, 2001). Overall, 17 of 26 (65%) of the primary HCC samples were methylated in the SOCS-1 CpG island. These results demonstrate that the methylation status of the SOCS-1 gene can be used to distinguish normal liver from hepatocellular carcinoma.

Constitutive JAK2 Activation in HCC Cells Containing Methylation Silenced SOCS-1

The functional consequence of SOCS-1 methylation-related silencing also was examined. Examination of the tyrosine phosphorylation status of JAK2 in HCC cell lines revealed that JAK2 was not phosphorylated in a cell line that was free of methylation in the CpG island and expressed SOCS-1, whereas two SOCS-1 methylation-silenced cell lines showed JAK2 phosphorylation (see FIG. 4a in Yoshikawa et al., supra, 2001). These results are consistent with JAK2 inhibition by SOCS-1, and with constitutive activation of JAK2 in cells exhibiting inactivation of SOCS-1 gene expression due to CpG island methylation.

To further determine the role of SOCS-1 in the JAK/STAT pathway, the phosphorylation status of STAT3 was examined. It was expected that JAK2 activation would result in constitutive STAT3 phosphorylation and, indeed, three cell lines (SNU-387, HuH-1, and PLC/PRF/5) that exhibited SOCS-1 inactivation and JAK2 phosphorylation also showed constitutive phosphorylation of STAT3 (see FIG. 4b in Yoshikawa et al., supra, 2001). In comparison, in two cell lines without SOCS-1 inactivation, one (HuH-7) had no constitutive phosphorylation of STAT3 and the other (SNU-182) showed STAT3 phosphorylation. This result indicates that, at least in the SNU-182 cell line, STAT3 is activated by pathways other than JAK2, which was not phosphorylated.

To confirm these results, cell lines were treated with the JAK2 specific inhibitor, AG490 (Meydan et al., *Nature* 379: 645-648, 1996, which is incorporated herein by reference). AG490 treatment led to a time dependent reduction in STAT3 phosphorylation in SOCS-1 inactivated (JAK2 activated) cell lines (SNU-387 and HuH-1), but not in the SOCS-1 expressing SNU-182 cells. These results demonstrate that SOCS-1 inactivation is associated with activation of the JAK/STAT pathway, including the well characterized STAT3 protein.

Growth Suppression by SOCS-1 Restoration

Because the JAK/STAT pathway may be an oncogenic pathway (Ihle et al., supra, 1995), the role of SOCS-1 in cell growth was examined. When a SOCS-1 expression vector was introduced into HCC cells exhibiting methylation-silenced SOCS-1 gene expression, the number of colonies of SOCS-1 transfected cells was substantially decreased as compared with HCC cells transfected with the control vector (see FIG. 5 in Yoshikawa et al., supra, 2001).

AG490 has been reported to suppress growth of B cell leukemia cells, in which JAK2 was constitutively activated (Meydan et al., supra, 1996). To test for the growth suppression by AG490, HCC cells exhibiting methylation silenced SOCS-1 gene expression were grown in the presence or absence of AG490. Incubation with AG490 effectively suppressed the growth of the SOCS-1 methylation-silenced cells as shown by a decreased number of colonies. This result confirms the constitutive activation of JAK2 in the SOCS-1 methylation-silenced HCC cell lines, and demonstrates that constitutive activation of the JAK/STAT pathway is associated with silencing of SOCS-1 by methylation in HCC.

To examine the mechanism of growth suppression by SOCS-1, SOCS-1 methylation-silenced cells were transiently transfected with the SOCS-1 expression vector, and the expression of SOCS-1, the presence of fragmented DNA, and the integrity of cell nuclei were examined using an antibody to a tag on the expressed SOCS-1 protein, the TUNEL assay, and DAPI staining, respectively. SOCS-1 expressing cells selectively demonstrated fragmented genomic DNA, whereas cells that were not transfected with SOCS-1 had intact nuclei (see FIG. 5 in Yoshikawa et al., supra, 2001). These results indicate that restoration of SOCS-1 selectively induces apoptosis in SOCS-1 methylation-silenced cells.

The effect of SOCS-1 restoration in HCC cells also was examined for growth in soft agar. A SOCS-1 methylation-silenced cell line transfected with the SOCS-1 expression vector, and incubated in soft agar added with selection medium for 4 weeks, showed decreased colony numbers compared with the control transfectants. These results indicate that SOCS-1 suppresses anchorage-independent growth and growth in monolayers, and that restoration of SOCS-1 expression suppresses cell growth by inducing apoptosis in HCC cells.

Aberrant methylation in the SOCS-1 CpG island was identified in 65% of primary HCC samples and was tightly linked to the silencing of gene expression. In addition, an alteration of the matrix attachment of the SOCS-1 locus was detected, thus associating the methylation and expression status and indicating that DNA methylation facilitates dynamic changes in chromatin structure. The high incidence of methylation-associated SOCS-1 gene inactivation in HCC indicates that SOCS-1 silencing is involved in the etiology of HCC.

Activation of the JAK/STAT pathway has been implicated in the promotion of cancer. For example, activation of *Drosophila* JAK caused hematopoietic neoplasia, and a self-activating STAT3 mutation caused cellular transformation and tumorigenicity in nude mice. In addition, constitutive activation of the JAK/STAT pathway was reported in transformed cells and cancer cells, and JAK2 was constitutively activated in B cell leukemia. In T cell lines, human T cell lymphotrophic virus (HTLV-1) infection constitutively activated JAK1, JAK3, STAT3 and STAT5, and the v-abl oncogene constitutively activated JAK1 and JAK3 in transformed murine pre-B cells; the v-abl protein was physically associated with JAK1 and JAK3 in these pre-B cells (Danial et al., *Science* 269:1875-1877, 1995). STAT3 constitutive activation also was reported in v-src, v-fps, and v-sis transformed mouse fibroblast cell lines, and in human breast carcinoma cell lines (Garcia et al., supra, 1997).

A differential pattern of STAT activation was observed among lymphoid, myeloid and lymphoma cells. STAT5 was predominantly activated in acute lymphoid leukemia, whereas STAT1 and STAT3 were activated in acute myeloid leukemia and Burkitt's lymphoma (Weber-Nordt et al., *Blood* 88:809-816, 1996). A role for the JAK/STAT pathway in oncogenesis also was suggested by liver regeneration experiments, in that STAT3 DNA binding activity was greatly increased in the remnant rat liver after partial hepatectomy, and STAT3 translocated into the nucleus (Cressman et al., Hepatology 21:1443-1449, 1995; Trautwein et al., *Gastroenterology* 110:1854-1862, 1996). Additional support for the role of SOCS-1 in hepatocytes comes from reports of SOCS-1 knock out mice, which die of liver degeneration and lymphoid deficiency between 2 and 3 weeks after birth (Starr et al., *Proc. Natl. Acad. Sci. USA* 95:14395-14399, 1998; Naka et al., *Proc. Natl. Acad. Sci. USA* 95:15577-15582, 1998).

As disclosed herein, SOCS-1 methylation silencing was associated with JAK2 constitutive activation in HCC cell lines, thus providing a means by which aberrant regulation of the JAK/STAT pathway is involved in oncogenesis. Stimulation of the JAK/STAT pathway by cytokines and growth factors results in transactivation of target genes. In normal cells, SOCS-1 is simultaneously activated and blocks JAK activation, leading to termination or attenuation of the signal. The results disclosed herein indicate that in cancer cells, SOCS-1 is silenced by methylation and, therefore, is unable to terminate the signal, resulting in constitutive JAK activation. As a result, SOCS-1 silenced cells can exhibit unopposed growth stimulation due, for example, to the action of cytokines, growth factors and hormones that stimulate the JAK/STAT pathway.

The present results indicate that SOCS-1 normally functions to suppress growth of hepatocytes, as revealed in the decreased growth of SOCS-1 restored HCC cells in monolayer and in soft agar culture. Further, apoptosis occurred in the SOCS-1 restored cells, thus accounting, at least in part, for the growth suppression. The growth suppression activity of SOCS-1 in the JAK/STAT pathway was further supported by the observation that AG490, a specific chemical JAK2 inhibitor, replaced SOCS-1 function. AG490 suppressed the growth of SOCS-1 silenced HCC cells, and reversed the constitutive phosphorylation of STAT3. Notably, AG490 does not suppress the growth of normal haematopoietic progenitor cells at concentrations similar to those used in the present studies (Meydan et al., supra, 1996), and, as disclosed herein, had no effect on normal liver cells.

A high incidence of the methylation of SOCS-1 and its functional significance indicate that SOCS-1 inactivation can be involved in other cancer, particularly those for which JAK/STAT is constitutively activated (see, for example, Garcia et al., supra, 1997; Meydan et al., supra, 1996; Weber-Nordt et al., supra, 1996). SOCS-1 also is a member of the CIS family, which includes several other members, including SOCS-2, SOCS-3 and CIS2, all of which are negative regulators of cytokine signal transduction, and the inactivation of which can be involved in the development of cancer similar to SOCS-1.

EXAMPLE 2

Methylation of SOCS-1 is Associated with Multiple Myeloma

This Example demonstrates that SOCS-1 gene methylation silencing also occurs in multiple myeloma (MM) cells.

Methods

Multiple Myeloma Patient and Control Samples

After informed consent was given, bone marrow (BM) specimens were aspirated during routine clinical assessment of 35 MM patients, who presented at the University Hospital Aachen, Germany between 1995 and 2000. MM diagnosis and staging classification were made in accordance with standard criteria (Durie, *Sem. Oncol.* 13:300-309, 1986). Two control bone marrow aspirates were obtained from patients with non-metastatic solid tumors or malignant lymphoma without bone marrow infiltration or hematopoietic dysfunction as part of the routine staging procedure. Peripheral blood (PB) samples were collected from five healthy volunteers. Mononuclear cells from BM and PB were separated by density gradient centrifugation prior to further analysis. Details of the lymphoma samples have been described (Katzenellenbogen et al., supra, 1999; Esteller et al., *J. Natl. Canc. Inst.* 94:26-32, 2002, each of which is incorporated herein by reference).

Cell Culture and Drug Treatment

HL60, U266 and Raji cell lines were obtained from the American Type Culture Collection. KG1a and K562 cell lines were obtained from the German Collection of Microorganisms and Cell Cultures. KG1a and HL60 cells were cultured in Iscoves's modified Dulbecco's medium (IMDM, Invitrogen Corp.) with 20% FCS (Gemini Bio-Products). U266 cells were cultured in RPMI 1640 (Invitrogen Corp.) with 15% FCS. K562 and Raji cells were cultured in RPMI 1640 with 10% FCS, and XG1 cells were cultured in IMDM with 20% FCS and 10 U/ml IL-6 (Roche).

For gene expression studies, U266 and XG1 cells were incubated in complete culture medium with a final concentration of 1.0 µM 5-azacytidine (Sigma). After 4 days, drug-treated and untreated cells were harvested and subjected to RNA extraction. In order to assess the sensitivity to AG490, cell lines K562, U266 and XG1 were incubated with or without a final concentration of 50 µM AG490 for 4 days prior to analysis. For STAT3 phosphorylation analysis, cell lines U266 and XG1 were initially starved for 16 hr in culture medium supplemented with only 1% FCS and no cytokine. Cells were then washed in cold PBS and resuspended in their appropriate complete medium with or without 50 µM AG490 and samples were harvested for protein analysis after 1 hr and 24 hr.

Sodium Bisulfite Treatment and Methylation-Specific Polymerase Chain Reaction

For SOCS-1 MSP analysis, approximately 1 µg of DNA was modified by treatment with sodium bisulfite and amplified using primers as described in Example 1. Normal DNA from PB was treated in vitro with SSS I methyltransferase (New England Biolabs) in order to generate a positive control for methylated alleles of SOCS-1 (Esteller et al. *Cancer Res.* 59:793-797, 1999, which is incorporated herein by reference).

RNA Isolation and Reverse Transcriptase Polymerase Chain Reaction (RT-PCR)

Total RNA was isolated using a commercially available kit (Qiagen) according to the manufacturer's instructions. Approximately 3 µg RNA per sample were reverse transcribed with SuperScript™ reverse transcriptase (Invitrogen). For PCR, 1 µl of the cDNA preparation was amplified using the following SOCS-1 primers:

```
5'-CCCGGAGCATGCGCGAGAGC-3',   (sense; SEQ ID NO: 16)
and
                              (antisense; SEQ ID NO: 17)
5'-TGCGGGCTCTGCTGCTGTGG-3';
``` and the following GAPDH primers:

```
                              (sense; SEQ ID NO: 18)
5'-GACCACAGTCCATGCCATCAC-3',
and
```

-continued (antisense; SEQ ID NO: 19)
5'-GTCCACCACCCTGTTGCTGTA-3'.

Reactions were hot-started at 95° C. for 5 min and held at 80° C. before addition of 1.25 U of Taq polymerase (Invitrogen Corp.). Temperature conditions for SOCS-1 were 26 cycles of 95° C., 30 sec; 64° C., 30 sec; and 72° C., 30 sec, followed by 1 cycle of 72° C. for 5 min; and for GAPDH 23 cycles of 95° C., 1 min; 63° C., 1 min; and 72° C., 1 min; followed by 1 cycle of 72° C. for 5 min.

Flow Cytometric Analysis of Apoptosis

Apoptosis was assessed by annexin V binding and counterstaining with propidium iodide (PI) using a commercially available kit (Pharmingen) according to the manufacturer's instructions. Fluorescence analysis was performed on a BD LSR flow cytometer (Becton Dickinson).

Western Blot Analysis

Cell lysis and western blot analysis for STAT3 phosphorylation were performed as described in Example 1 (see, also, Yoshikawa et al., supra, 2001).

Results

SOCS-1 Methylation Status in Hematopoietic Cell Lines and Normal Tissues

SOCS-1 methylation status was analyzed by MSP in various human hematopoietic cell lines. SOCS-1 hypermethylation was observed in both IL-6-dependent MM cell lines, U266 and XG1, and in the AML cell line, KG1a (see, also, Example 3). In comparison, no aberrant methylation was observed in the HL60 AML cell line, or in the K562 chronic myelogenous leukemia (CML) cell line, or the Burkitt's lymphoma cell line (Raji); and no SOCS-1 methylation was found in normal peripheral blood mononuclear cells (PB-MNC; n=5) or in non-malignant bone marrow cells (n=2).

SOCS-1 Expression in MM Cell Lines

The MM cell lines were examined by semi-quantitative RT-PCR. XG1 cells require the addition of exogenous IL-6 (Zhang et al., *Blood* 83:3654-3663, 1994), whereas U266 cells depend on an IL-6 autocrine loop (Schwab et al., *Blood* 77:587-593, 1991). Despite the presence of IL-6 in the cell culture medium, the MM cell lines showed low (U266) or undetectable (XG1) SOCS-1 transcript levels. In comparison, normal PBMNC incubated in IMDM with 20% FCS and 10 U/ml IL-6 for 2 hr showed strong SOCS-1 expression; unstimulated PBMNC expressed only low levels of SOCS-1. Incubation of U266 and XG1 cells with 1 µM 5-azacytidine for 96 hr resulted in reactivation of SOCS-1 gene expression in both MM cell lines, confirming that methylation was responsible for the loss of SOCS-1 expression in the MM cells.

Sensitivity of Hematopoietic Cell Lines to AG490

In order to investigate the activation of the JAK/STAT pathway in the context of methylation-silencing of SOCS-1 in hematopoietic cell lines, K562, U266 and XG1 cells were treated with 50 µM AG490 and the percentage of apoptotic cells after 96 hr was detected by annexin V binding and PI counterstaining. AG490 treatment induced apoptosis in U266 and XG1 cells, but had only a small effect on K562 cells. These results indicate that cell lines that carry a hypermethylated SOCS-1 gene, including MM cells and HCC cells (see Example 1) have a greater sensitivity to apoptosis induction by AG490 as compared to cell lines without SOCS-1 hypermethylation.

STAT3 Phosphorylation

AG490 treatment also inhibited STAT3 phosphorylation in U266 cells, while there were only minor effects in XG1 cells. These results demonstrate that, in addition to inducing apoptosis in the MM cell lines, AG490 treatment also results in inhibition of STAT3 phosphorylation, which represents a downstream event in the JAK/STAT pathway.

SOCS-1 Methylation in Primary Patient Samples

SOCS-1 methylation status also was examined by MSP in primary patient samples. Aberrant methylation was present in 62.9% (23/35) of MM cases. Since IL-6 is involved in B cell growth and differentiation into plasma cells, and acts as a survival factor in MM pathogenesis, an association of methylation-silencing of SOCS-1 with other lymphoid malignancies was examined. MSP analysis of malignant lymphomas of various histologies, including 55 B cell lymphomas, 4 T cell lymphomas, and 3 Hodgkin's lymphomas revealed SOCS-1 hypermethylation in only 3.2% (2/62) of the samples, including one large B cell lymphoma and one T lymphoblastic lymphoma.

Stimulation of the JAK/STAT pathway by cytokines or growth factors such as IL-6 results in transactivation of target genes. Under physiological conditions, SOCS-1 is simultaneously up-regulated and blocks JAK activation, leading to termination or attenuation of the signal. If hypermethylation-associated transcriptional silencing of SOCS-1 occurs in tumor cells, this negative feedback loop is disrupted, and the cells can become more responsive to stimulation by cytokines and growth factors that use the JAK/STAT pathway for signal transduction. In MM pathogenesis, IL-6 has been identified as an essential growth and survival factor. As such, loss of SOCS-1 function can result in increased IL-6 signal transduction, and support survival and expansion of MM cells.

As disclosed herein, the IL-6-dependent MM cell lines U266 and XG1 exhibited aberrant SOCS-1 hypermethylation that is associated with transcriptional silencing, and treatment of these cell lines with the demethylating agent, 5-azacytidine, resulted in re-expression of SOCS-1. The importance of JAK activation in cell lines containing a hypermethylated SOCS-1 gene was demonstrated by their sensitivity to the chemical JAK inhibitor, AG490. These results are in accordance with the finding that, in HCC cell lines, silencing of SOCS-1 by hypermethylation was associated with constitutive activation of JAK2 (Example 1). AG490 also resulted in inhibition of STAT3 phosphorylation in U266 cells, similar to the effect described in the MM cell line, XG2 (see De Vos et al., *Brit. J. Haematol.* 109:823-828, 2000, which is incorporated herein by reference).

Aberrant methylation within the SOCS-1 CpG island was identified in 62.9% of MM patient samples, but in only 3.2% of primary tissues from different malignant lymphomas. This finding is in accordance with the importance of the JAK/STAT pathway, particularly IL-6 signaling, in MM pathogenesis compared to other lymphoid neoplasms. Previous molecular studies have focused primarily on genetic aberrations in MM, wherein changes that were detected included chromosomal translocations involving the immunoglobulin heavy chain locus on chromosome 14q32 and various partner genes such as cyclin D1, cyclin D3, fibroblast growth factor receptor 3 and c-maf, as well as mutations of N-ras and K-ras (see Hallek et al., *Blood* 91:3-21, 1998, Kastrinakis et al., *Ann. Oncol.* 11: 1217-1228, 2000). Hypermethylation of $p15^{INK4B}$, $p16^{INK4A}$, and DAP-kinase also has been identified in MM patients and cell lines (Ng et al., supra, 2001; Ng et al., *Blood* 89:2500-2506, 1997; Urashima et al., *Clin. Cancer Res.* 3:2173-2179, 1997; Tasaka et al., *Brit. J. Haematol.*

101:558-564, 1998; Guillerm et al., *Blood* 98:244-246, 2001), demonstrating that epigenetic silencing of genes that effect cell cycle regulation and apoptosis pathways is an additional mechanism of gene inactivation in MM.

The results disclosed herein reveal the presence of an important epigenetic event in the pathogenesis of MM. Methylation-silencing of SOCS-1 gene expression can result in increased responsiveness of the neoplastic clone to IL-6 signaling, thus supporting survival and expansion of MM cells. As such, the present results not only provide an insight into the pathogenesis of MM, but, because hypermethylation-associated gene silencing is a reversible phenomenon, also provide indications for treating MM (Cameron et al., *Nat. Genet.* 21:103-107, 1999). For example, demethylating agents such as 5-azacytidine, which are clinically effective in patients with AML and myelodysplastic syndrome (see, for example, Willemze et al., *Leukemia* 11 (Suppl. 1):S24-27, 1997, describing an EORTC Leukemia Cooperative Group phase II study (06893); Wijermans et al., *J. Clin. Oncol.* 18:956-962, 2000, describing a multicenter phase II study in elderly patients, each of which is incorporated herein by reference), are now indicated for treatment of MM patients having methylation-silenced SOCS-1 gene expression.

The high prevalence of SOCS-1 hypermethylation in MM indicates that this pathway can be targeted for therapeutic intervention. While reactivation of genes like $p15^{INK4B}$ and $p16^{INK4A}$ can contribute to reconstitution of disrupted cell cycle regulation, reactivation of SOCS-1 can functionally restore the endogenous negative feedback loop of IL-6 signaling. Since IL-6 contributes to MM resistance to conventional therapy options such as corticosteroids, inhibition of IL-6 signaling by SOCS-1 reactivation can be used to overcome such resistance.

The recognition that IL-6 is a survival factor for MM cells has prompted the development of strategies to block its effects therapeutically, for example, using anti-IL-6 monoclonal antibodies or antisense oligonucleotides. As an alternative approach, in MM cases in which SOCS-1 is silenced by hypermethylation, treatment with demethylating agents can be used to reconstitute the function of SOCS-1 as a physiological suppressor of IL-6 signaling. Thus, the combination of demethylating agents with conventional therapeutics or tyrosine kinase inhibitors can provide a promising new strategy in MM therapy.

EXAMPLE 3

Methylation of SOCS-1 is Associated with Leukemia

This Example demonstrate that hypermethylation of the SOCS-1 gene also is associated with acute leukemias.

Methods

Primary Leukemia Samples

Adult leukemia were obtained from the University Hospital Aachen, Germany. The pediatric have previously been described for inactivation at the INK4A and INK4B locus (Herman et al., supra, 1997).

Cell Culture and Drug Treatment

HL60 cells were obtained from the American Type Culture Collection and KG1a cells from the German Collection of Microorganisms and Cell Cultures. Both cell lines were routinely cultured in IMDM (Invitrogen Corp.) with 20% FCS (Gemini Bio-Products). In order to assess the sensitivity to AG490, HL60 and KG1a cells were incubated with or without a final concentration of 50 µM AG490 (Sigma) for 96 hr prior to analysis.

Flow Cytometric Analysis of Apoptosis

The percentage of apoptotic cells was determined by annexin V-binding and counterstaining with propidium iodide (PI), and fluorescence analysis was performed as described in Example 2.

Methylation Specific PCR

MSP was performed as described in Example 1. The methylation specific primer sequences were as follows:

```
                                      (forward; SEQ ID NO: 2)
5'-TTCGCGTGTATTTTTAGGTCGGTC-3',
and
                                      (reverse; SEQ ID NO: 3)
5'-CGACACAACTCCTACAACGACCG-3'.
```

The unmethylation specific primer sequences were as follows:

```
                                      (forward; SEQ ID NO: 4)
5'-TTATGAGTATTTGTGTGTATTTTTAGGTTGGTT-3',
and
                                      (reverse; SEQ ID NO: 5)
5'-CACTAACAACACAACTCCTACAACAACCA-3'.
```

Western Blot Analysis

Western blot analysis was performed as described in Example 1. Blots were stained using anti-phospho-STAT1, anti-phospho-STAT3 or anti-phospho-STAT5 antibody (New England Biolabs) to detect tyrosine phosphorylation of STAT protein. After removing the antibody, the blot was analyzed using anti-STAT1, anti-STAT3 or anti-STAT5 antibody, respectively (BD Transduction Laboratories).

Results

Methylation of SOCS-1 CpG Island in Acute Leukemia.

SOCS-1 CpG island methylation was examined in 38 pediatric leukemia and 51 adult leukemia samples. The 38 pediatric leukemia included 17 acute myeloid leukemia (AML), 8 T cell ALL (T-ALL) and 13 B cell ALL (B-ALL). The 51 adult leukemia included 37 de novo AML and 14 AML transformed from myelodysplastic syndrome (MDS). The overall frequency of SOCS-1 methylation was 31% (28 of 89). In pediatric leukemia, methylation was detected in 6 of 17 (35%) AML, 2 of 8 (25%) T-ALL and 2 of 13 (15%) B-ALL; and for adult leukemia, methylation was detected in 11 of 37 (30%) de novo AML and 7 of 14 (50%) secondary AML transformed from MDS. No methylation was detected in 2 MDS samples without transformation. Methylation of SOCS-1 was found in all subtypes of AML (M0-M7).

Effect of JAK/STAT Inhibition in Leukemia

The effect of SOCS-1 methylation on inhibition of JAK/STAT pathway in leukemia was examined. Treatment of the AML cell line, KG1a, which was methylated in the SOCS-1 CpG island, with AG490 induced apoptosis, whereas treatment of the AML line, HL60, in which SOCS-1 was not methylated, had no effect, as determined by annexin V binding and PI counterstaining. These results demonstrate that the leukemia cell line with a hypermethylated SOCS-1 gene showed greater sensitivity to AG490 as compared to cells without SOCS-1 hypermethylation.

The effect of AG490 on STAT activation in the SOCS-1 methylated cells also was examined following treatment with AG490. Constitutive activation of STAT1, STAT3 and STAT5 was detected in the cell line with SOCS-1 methylation prior to treatment with AG490, whereas, following treatment with AG490, tyrosine phosphorylation of STAT3 and, particularly, of STAT1 decreased; no change was observed in the tyrosine phosphorylation of STAT5.

These results demonstrate that hypermethylation of the SOCS-1 gene also is associated with acute leukemia, and that, in addition to genetic alterations, activation of the JAK/STAT pathway in leukemias is associated with an epigenetic change. Hypermethylation-associated silencing of SOCS-1 can increase activation of the JAK/STAT signal transduction pathway, thus supporting the growth of leukemia cell clones. The importance of the JAK/STAT pathway in KG1a cells, which contain a hypermethylated SOCS-1 gene, is underscored by their sensitivity to AG490, which inhibits JAK activity. In contrast, AG490 showed only weak induction of apoptosis in HL60 cells, which have an unmethylated SOCS-1 gene but contain an activating N-ras mutation. Previous reports have demonstrated the effectiveness of AG490 in the treatment of ALL (Meydan et al., *Nature* 379: 645-648, 1996). The importance of SOCS-1 inactivation in hematological malignancies is supported by reports that SOCS-1 suppresses the expansion of immature thymocytes (Trop et al., *Blood* 97: 2269-2277, 2001), and that AG490 induces apoptosis in myeloma cells (De Vos et al., *Brit. J. Haematol.* 109: 823-828, 2000; Catlett-Falcone et al., supra, 1999) and leukemic Sezary cells (Eriksen et al., *Leukemia* 15: 787-793).

Aberrant methylation of the SOCS-1 CpG island was detected in many different subtypes of acute leukemia, with no marked difference between pediatric and adult leukemias. Methylation of SOCS-1 occurred in 31% of de novo AML, 50% in secondary AML, 25% in T ALL, and 15% in B ALL cases. Thus, SOCS-1 methylation occurs with similar incidence in all 3 types of de novo acute leukemia, although the secondary AML demonstrated a relatively higher incidence. These results indicate that SOCS-1 methylation is ubiquitous among acute leukemia, and that the involvement of the JAK/STAT signal transduction pathway is significant in the development of hematological malignancies. The secondary AML transformed from MDS showed the higher methylation incidence than de novo leukemia, and 2 of 2 MDS without transformation were free from the aberrant methylation. The distribution of SOCS-1 methylation also was analyzed among subtypes of AML in adult. One or 2 positive samples appeared in most of the subtypes both in de novo and secondary AML, further indicating that SOCS-1 methylation occurs in various cell types. Together with the similar occurrence among AML, T ALL and B ALL, these results indicate that SOCS-1 methylation can be used as a marker for any kind of acute leukemia.

Although the invention has been described with reference to the above examples, it will be understood that modifications and variations are encompassed within the spirit and scope of the invention. Accordingly, the invention is limited only by the following claims.

What is claimed is:

1. A method for selecting an agent for treating a cancer patient, the method comprising
   detecting decreased expression of SOCS-1 gene product due to methylation of a cytosine residue of a CpG dinucleotide in a CpG island of a suppressor of cytokine signaling-1 (SOCS-1) gene in a sample comprising cancer cells from the patient; and selecting an agent that restores the expression of the SOCS-1 gene product in the cancer cells.

2. The method of claim 1, wherein the SOCS-1 gene product is encoded by SEQ ID NO:1.

3. The method of claim 1, wherein the agent comprises a demethylating agent.

4. The method of claim 3, wherein the demethylating agent comprises 5-aza-2'-deoxycytidine.

* * * * *